US007851213B2

(12) United States Patent
Berinstein et al.

(10) Patent No.: US 7,851,213 B2
(45) Date of Patent: Dec. 14, 2010

(54) TUMOR ANTIGENS BFA4 AND BCY1 FOR PREVENTION AND / OR TREATMENT OF CANCER

(75) Inventors: Neil Berinstein, Toronto (CA); Corey Lovitt, Bolton (CA); Mark Parrington, Bradford (CA); Artur Pedyczak, Pickering (CA); Laszlo Radvanyi, Richmond Hill (CA); Scott Gallichan, Campbellville (CA); Devender Singh-Sandhu, Thornhill (CA); Raymond P. Oomen, Aurora (CA); Shi-Xian Cao, Stouffville (CA)

(73) Assignee: Sanofi Pasteur Limited, North York, Ontario (CA)

( * ) Notice: Subject to any disclaimer, the term of this patent is extended or adjusted under 35 U.S.C. 154(b) by 1471 days.

(21) Appl. No.: 10/611,440

(22) Filed: Jul. 1, 2003

(65) Prior Publication Data

US 2004/0197912 A1    Oct. 7, 2004

Related U.S. Application Data

(60) Provisional application No. 60/394,346, filed on Jul. 3, 2002, provisional application No. 60/394,503, filed on Jul. 9, 2002, provisional application No. 60/411,833, filed on Sep. 18, 2002, provisional application No. 60/445,342, filed on Feb. 6, 2003.

(51) Int. Cl.
*C12N 15/00* (2006.01)
*A61K 48/00* (2006.01)
(52) U.S. Cl. .................. 435/320.1; 424/93.2; 424/93.6
(58) Field of Classification Search ........................ None
See application file for complete search history.

(56) References Cited

U.S. PATENT DOCUMENTS 5,833,975 A * 11/1998 Paoletti et al. ............. 424/93.2
6,780,586 B1     8/2004 Gish et al.
7,217,421 B1 *  5/2007 McArthur et al. ......... 424/277.1

FOREIGN PATENT DOCUMENTS

WO    WO 02/00677    *  1/2002
WO    WO 03/084467   * 10/2003

OTHER PUBLICATIONS

Tartaglia et al, Vaccine, 2001, vol. 19, pp. 2571-2575.*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkinl ("Report and Recommendation of the Panel to Assess the NIH Investment in Research on Gene Therapy", NIH, 1995).*
Abstract of Algarra et al International Journal of Clinical and Laboratory Research, 1997, vol. 27, pp. 95-102).*
Bodey et al (Anticancer Research, Jul.-Aug. 2000, vol. 20, pp. 2665-2676).*
Lauritzsen et al (International Journal of Cancer, 1998, vol. 78, pp. 216-222).*
Sarma et al (Journal of Experimental Medicine, 1999, vol. 189, pp. 811-820).*
Paul, Fundamental Immunology, (text), 1993.*
Apostolopoulos et al (Nature Medicine, 1998, vol. 4, pp. 315-320).*
Jager et al (PNAS, 2000, vol. 97, pp. 12198-12203).*
Semino et al (Journal of Biological Regulators and Homeostatic Agents, 1993, vol. 7, pp. 99-105.*
Ohlen et al (Journal of Immunology, 2001, vol. 166, pp. 2863-2870).*
Antoinia et al (International Immunology, 1995, vol. 7, pp. 715-725).*
Yu and Restifo (Journal of Clinical Investigation, 2002, vol. 110, pp. 289-294.*
Lee et al (Journal of Immunology, 1999, vol. 163, pp. 6292-6300).*
Abstract of Wheeler (Salud p'ublica de M'exico, (Jul.-Aug. 1997) 39 (4) 283-7).*
Efferson et al (Anticancer Research, 2005, vol. 25, pp. 715-724).*
Bachman et al (Journal of Immunology, 2005, vol. 175, pp. 4677-4685).*
Ghose et al (Human Gene Therapy, 2000, vol. 11, pp. 1289-1301).*
Schultze et al (Trends in Immunology, 2004, vol. 25, pp. 659-664).*
Le Fur et al (PNAS, 1997, vol. 94, pp. 7561-7565).*
Finke et al, Immunology Today, 1999, vol. 20, pp. 158-160.*
Donnelly et al (Journal of Immunology, Jul. 15, 2005, 175(2):633-639.*
Vanniasinkam et al (Journal of Clinical Virology, Aug. 2006, 36(4):292-297).*
Young et al (Journal of Pathology, 2006, vol. 208, pp. 299-318).*
NCI GenBank database Accession No. AF183810, "*Homo sapiens* zinc finger transcription factor TRPS1 mRNA, complete cds."
NCI GenBank database Accession No. AAF23614, "zinc finger transcription factor TRPS1 [*Homo sapiens*]".
Momeni, P. et al. Mutations in a new gene, encoding a zinc-finger protein, cause tricho-rhino-phalangeal syndrome type I. Nat Genet 24, 71-4 (2000).
Malik, et al. Deletion of the GATA domain of TRPS1 ... Mol. Cell. Biol. 22, 8592-600 (2002).
Ludecke, H.J. et al. Genotypic and phenotypic spectrum in tricho-rhino-phalangeal syndrome types I and III. Am J Hum Genet 68, 81-91 (2001).
Kaiser, F.J. et al. Novel missense mutations in the TRPS1 transcription factor define the nuclear localization signal. Eur J Hum Genet 12, 121-6 (2004).
Ginestier, C. et al. Distinct and complementary information ... Am J Pathol 161, 1223-33 (2002).
Kobayashi, H. et al. Missense mutation of TRPS1 in a family of tricho-rhino-phalangeal syndrome type III. Am J Med Genet 107, 26-9 (2002).

(Continued)

*Primary Examiner*—Karen A Canella
(74) *Attorney, Agent, or Firm*—Patrick J. Halloran

(57) ABSTRACT

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

32 Claims, 6 Drawing Sheets

OTHER PUBLICATIONS

Gentile, et al. A novel mutation in exon 7 in a family with mild tricho-rhino-phalangeal syndrome type I. Clin Genet 63, 166-7 (2003).

Hatamura, I. et al. A nonsense mutation in TRPS1 in a Japanese family with tricho-rhino-phalangeal syndrome type I. Clin Genet 59, 366-7 (2001).

Chang, G.T. et al. Differentially expressed genes in androgen-dependent and -independent prostate carcinomas. Cancer Res 57, 4075-81 (1997).

Kunath, M., Ludecke, H.J. & Vortkamp, A. Expression of Trps1 during mouse embryonic development. Mech Dev 119 Suppl 1, S117-20 (2002).

Malik, T.H. et al. Transcriptional repression and developmental functions of the atypical vertebrate GATA protein TRPS1. Embo J 20, 1715-25 (2001).

Chang, G.T. et al. Characterization of a zinc-finger protein and its association with apoptosis in prostate cancer cells. J Natl Cancer Inst 92, 1414-21 (2000).

Kaiser, et al. The RING finger protein RNF4, a co-regulator of transcription, interacts with the TRPS1 transcription factor. J Biol Chem 278, 38780-5 (2003).

Tremblay, J.J. & Viger, R.S. Novel roles for GATA transcription factors in the regulation of steroidogenesis. J Steroid Biochem Mol Biol 85, 291-8 (2003).

Savinainen, et al. Expression and copy number analysis of TRPS1, EIF3S3 and MYC genes in breast and prostate cancer. Br. J. Cancer 90, 1041-1046 (2004).

Williams, et al. Analysis of differential protein expression in normal and neoplastic human breast epithelial cell lines. Electrophoresis, 19: 333-343 (1998).

DeRisi, et al. Use of a cDNA microarray to gene expression patterns in human cancer. Nature Genetics 14: 457-460 (1996).

Welford, et al. Detection of differentially expressed genes in primary tumor tissues . . . Nucleic Acids Research 26(12): 3059-3065 (1998).

Khan, et al. Expression profiling in cancer using cDNA microarrays. Electrophoresis 20: 223-229 (1999).

Radvanyi, et al. The gene associated with trichorhinophalangeal syndrome in humans is overexpressed in breast cancer. PNAS 102(31): 11005-11010 (2005).

* cited by examiner

FIGURE 1

```
ATGGTCCGGAAAAAGAACCCCCTCTGAGAAAGTTGCAAGTGAAGGCGAAGGGCCAGATCCTGAGCCTATAGGTACAGAAAGCAAGGTATCTGGAAAGAACAAGAATTCTCTGCAGA
TCAGATGTCAGAAATAAGACGGATCAGAGTGATGCTCAGAACTAAATCATAAGGAGGAACATAGCTTGCATGTTCAGATCCATCTTCTAGCAGTTGCAAGAAGGACTTGAAAGCCAGTTC
TGAGTGAGAAGGCTGGCTTGAAGTCTCCCAGTAAGGACGAGAGCCAGTAAGGAGGAAACTTTCCCTCCTTCCGCATGATGAGGTGACAGACAGAAATATGTTGGCTTTCTCATTTCCAGCTGCTGGG
GGAGTCTGTGAGCCCTTGAAGTCTCTGAGCCCTCAAGAGACAGAGGCCAGATGACCCTCAAGATATGCCTGCACCCCCCTCAGGGAGCTCACTGGAGACAAAGGAAGATCAGAAGATGTCACCAAA
GGCTACAGAGGAAACAGGGCAAGCACAGAGTGGTTCAAGCCAATTGTCAAGGTTTGAGCCCACCTCTGTCTCAGAGACTTTGCAGACTTTCAGGACTTTGCAAGGCCTCAAAAAACCCACAAGTGCCTTCAGATGGGGTGTAAGACTGAATA
AATCCAAAACTGACTTGAATGACAACCAGACCCGGCACCCGGCCAATTGTCAAGGCCACCTCTGTCTCCAGAGCTTTGCAGACTTTGCAGACTTTGAATATCGTTGCATATCGTGGATATGCATAACACCACAGAT
CTGATTAAGCACTTCCGAAAGTATCACTTAGGACTGCATAACCGACTGCATAAACCGGCATAAGGGCATGCATGTGCATGCGGAATATGCCAATAACATGGCCTGTGTTTACTAAACTTCACTTAACATGTGCAGGTGCAGTTCAGCCATTCCAAAGA
CTTCCAGAAGGTCAACCGTTCTGTGTTCTCGTGTGCGAGGACACCAAGTATATTCCGCTGTAAATTCGCAATTCTCAAAACTCACTTATATGGGACCTATATGCAGGCCCATAGACAAAATTCACCCAGAATAGACAACAATTTCTTCAGACT
GCATTGGACGGAAACACCAGATTGCCAAGGACAACACCACAGCTTCTCCCCTCTGAGTTGCAAAACCTTCAGTGGTACTCAGTGCCATAAACCTCAGAGCGCCCTCTTTAAGACCCCTGATTTCTGGGTACTCAGGCGCCACCAGTTACTACTGTGTA
GCAGGACAAGATAACAGTCAAAGCAGGAGAAGATGACATGCAGAAGCCATGGCAAGCACAAGACAGACAATGACCCCTGATGTAATTGTAGTGTGGGCTAAAAGAAGGACTTCTCCGTCATTATCCAGCAACAGCTCCATAACA
AATTTTGTAGTTCAGCTGTGAGTCATCAGAATGATATCTAGAAACTGCTAAAACTGGTACATGGCAAGCAGACAATGACCCCTGATGTAATTGTAGTGGGGCTAAAAAGAAGGACTTCTCCGTCATTATCCAGCAACAGCTCCATAACA
AGGGGCTCTGTCATTAATCGAGCTATAAACACTGTCATTCTGTCCTGGCGCCTGAGTCAAACATCAGTGTCAAAGGATCGAGCCAGTGGCATCTGCAAGGATCGGATGGCAGCTGTTTACAGCTGCCGATATGACTCAGTCAGTTTCAGTGACCACTTCAACACTGTT
TTCAAGTGTACCATTAAACGTATAATTGTCATTCTGTCCCTGGCGCCTGAGTCAAACATCAGTGTCAAAGGATCGAGCAGTGGCATCTGCAAGGATCGTACAAATGCCATATCCACCATCAAAGAGAACAAGCCCAAAATTGACTTCAGGGTCTACAATCTGCTAACTCCAGACTC
GCACTCTGCTTCTGCACTTGTCTCTGGGCGCTGGAAGCTCGGAGTCAAACATCAGTGTTCATTGCAAGGATGTCAAAGGATCGTACAAATGCCATATCCACCATCAAAGAGAACAAGCCCAAAATTGACTTCAGGGTCTACAATCTGCTAACTCCAGACTC
TGTCATGAGTCCAAGGACTACAGGACCACTACGACCAACGGCACACAGTCCTGAGAGTGTGGTGAAGAGAGAGAAGCTGGTGAAGACCTGGGAACCAAGGATTCCTCGCAGCCTGTGTCTCTGCAGCCCTGTCTGTAACCATCATTAAACATCATTAAACAAAACAACGGTTTAGGAGGAGAACAAGAAGCGC
CCCAAGTGGAAGAGAGATTTCTGAGAGTGTGGTGAAGAGAGAGAAGCTGGTGAAGACCTGGGAACCAAGGATTCCTCGCAGCCTGTGTCTCTGCAGCCCTGTCTGTAACCATCATTAAACATCATTAAACAAAACAACGGTTTAGGAGGAGAACAAGAAGCGC
CACTGCCAGGAACAGATCACTCTGGGCGCCAGTTCCTGGCGCCGACATCTGGGCGCCGACATCTTATGGCTTGGCTGTGGAAGAGCGCGTAGAGGGTCGACTCCCAGGCTTCACTGACTTCACTGACTTCACTGACTTCACTGACTTCACTGACTTCACTGACTTCACTGACTTCACTGACTTCACTGACTTCACT
TAAAATGGAGAGGCAGACATCCTGGGCGCCGACATCTTATGGCTTGGCTGTGGAAGAGCGCGTAGAGGGTCGACTCCCAGGCTTCACTGACTTGCCGCAGCCAAGGCAATGACTAAAACAAAACAACAAGCCCGTTAGAGGAGGTCAGCAGCCAAGGAATGACTAACTGAAAGTCA
GAGGCCGCCCATCTGGGCGCCGACATCTTATGGCTTGGCTGTGGAAGAGCGCGTAGAGGGTCGACTCCCAGGCTTCACTGACTTGCCGCAGCCAAGGCAATGACTAAAACAAAACAACAAGCCCGTTAGAGGAGGTCAGCAGCCAAGGAATGACTAACTGAAAGTCA
GGGAGAAAACAAGTCCAAGGATGAATCCAGTCCTGGCGCCGACATCTTATGGCTTGGCTGTGGAAGAGCGCGTAGAGGGTCGACTCCCAGGCTTCACTGACTTGCCGCAGCCAAGGCAATGACTAAAACAAAACAACAAGCCCGTTAGAGGAGGTCAGCAGCCAAGGAATGACTAACTGAAAGTCA
GCGGATATGTCAACGGCACTTCAGGCTGACGCTGTGCCTCCAGCCTAAGAAGTCCTCACCAGCTAACAACAGCAGGCCCAGGGTCATTGACTAAAATACGAAAGTACCAGGAAAGTAGTCATGGAGATCTGAGGACTTCAGCCAGCCAGTCGTCAGCCAAAACTGAAGAACAAGAA
CTTAACCCAGGCCACTCACTCCAGCTAAGAAGTCCTCACCAGCTAACAACAGCAGGCCCAGGGTCATTGACTAAAATACGAAAGTACCAGGAAAGTAGTCATGGAGATCTGAGGACTTCAGCCAGCCAGTCGTCAGCCAAAACTGAAGAACAAGAACTCAACAAGGA
CCAGAGAAATTCCACTCCAGCTAAGAAGTCCTCACCAGCTAACAACAGCAGGCCCAGGGTCATTGACTAAAATACGAAAGTACCAGGAAAGTAGTCATGGAGATCTGAGGACTTCAGCCAGCCAGTCGTCAGCCAAAACTGAAGAACAAGAACTCAACAAGGA
TGCAACCTTTGCACATTGACATTCAGATAAAATTATTCACACAGCCCCAAATTATTCACACAGCCCCAAATATCGGAAATAGTCCTCAGGAAATAGTTCATCCGTATCGAAGGAAAGTTCATGAGAGGCAGTCCAGAGTGACTTCTATAGAAAAGTAC
ATGAGACCTGCGAGTAAACACCCAAATATTCACACAGCCCCAAATATCGGAAATAGTCCTCAGGAAATAGTTCATCCGTATCGAAGGAAAGTTCATGAGAGGCAGTCCAGAGTGACTTCTATAGAAAAGTACTCCAGAGTGAAGCTGATTGGCT
GCGGTTCGGAGTAAATATAAGCTCTCCGTTCCTGGAATCGCACTACTTGAGTTGGGATCAGAGACATTGGATCAGAAAGCATTCCAAGATAGGCCCAACGTGCCTCAAGGAGAAACGTGCCTCAAGGAGAAACGAAGGCACCACCAAAT
CTCATTTTTCAGCTGTTGATGATCAGAGAGACAATTCCTCAACAATGACATTGGGATCAGAGACATTGGATCAGAAAGCATTCCAAGATAGGCCCAACGTGCCTCAAGGAGAAACGTGCCTCAAGGAGAAACGAAGGCACCACCAAAT
GTAAAATGAAGGTCCCTTGAATGTAGTAAACAGAGAAGAGTTGATAGAAGATACGACATTCAAGTAACTTCAACAAATGAACTTTCAACAAATGTGCACTGTGGCATTGTTCTGATGAAGTGATGTA
TGCTTTGCATATGAGTTGCATGGTGACAGTGACCTTTCAGTGCAGCATATGCCAGCACATATCGAGCAGCACATATCGAGCAGCACATATCGAGCAGCACATATCGAGCAGCACATATCGAGCAGCATATCCAGCAGGACAACATATGACTTCACAACACATATGACTTCACAACACATATGACTTCACAACACATATGACTTCACAACACATATGACTTCAGAGGGGCCTGCATAGAACA
ATGCACAAGTGAAAAAATGAAAAAAATGGAAAAACCTAAAGAGT TAA*
```

FIGURE 2

MVRKKNPPLRNVASEGEGQILEPIGTESKVSGKNKEFSADQMSENTDQSDAAELNHKEEHSLHVQDPSSSKKDLKSAVLSEKAGFNYE
SPSKGGNFPSFPHDEVTDRNMLAFSFPAAGGVCEPLKSPQRAEADDPQDMACTPSGDSLETKEDQKMSPKATEETGQAQSGQANCQGLS
PVSVASKNPQVPSDGGVRLNKSKTDLLVNDNPDPAPLSPELQDFKCNICGYGYYGNDPTDLIKHFRKYHLGLHNRTRQDAELDSKILAL
HNMVQFSHSKDFQKVNRSVFSGVLQDINSSRPVLLNGTYDVQVTSGGTFIGIGRKTPDCQGNTKYFRCKFCNFTYMGNSSTELEQHFLQ
THPNKIKASLPSSEVAKPSEKNSNKSIPALQSSDSGDLGKWQDKITVKAGDDTPVGYSVPIKPLDSSRQNGTEATSYYWCKFCSFSCES
SSSLKLLEHYGKQHGAVQSGGLNPELNDKLSRGSVINQNDLAKSSEGETMTKTDKSSSGAKKKDFSSKGAEDNMVTSYNCQFCDFRYSK
SHGPDVIVVGPLLRHYQQLHNIHKCTIKHCPFCPRGLCSPEKHLGEITYPFACRKSNCSHCALLLHLSPGAAGSSRVKHQCHQCSFTT
PDVDVLLFHYESVHESQASDVKQEANHLQGSDGQQSVKESKEHSCTKCDFITQVEEEISRHYRRAHSCYKCRQCSFTAADTQSLLEHFN
TVHCQEQDITTANGEEDGHAISTIKEEPKIDFRVYNLLTPDSKMGEPVSESVVKREKLEEKDGLKEKVWTESSSDDLRNVTWRGADILR
GSPSYTQASLGLLTPVSGTQEQTKTLRDSPNVEAAHLARPIYGLAVETKGFLQGAPAGGEKSGALPQQYPASGENKSKDESQSLLRRRR
GSGVFCANCLTTKTSLWRKNANGGYVCNACGLYQKLHSTPRPLNIIKQNNGEQIIRRRTRKRLNPEALQAEQLNKQQRGSNEEQVNGSP
LERRSEDHLTESHQREIPLPSLSKYEAQGSLTKSHSAQQPVLVSQTLDIHKRMQPLHIQIKSPQESTGDPGNSSSVSEGKGSSERGSPI
EKYMRPAKHPNYSPPGSPIEKYQYPLFGLPFVHNDFQSEADWLRFWSKYKLSVPGNPHYLSHVPGLPNPCQNYVPYPTFNLPPHFSAVG
SDNDIPLDLAIKHSRPGPTANGASKEKTKAPPNVKNEGPLNVVKTEKVDRSTQDELSTKCVHCGIVFLDEVMYALHMSCHGDSGPFQCS
ICQHLCTDKYDFTTHIQRGLHRNNAQVEKNGKPKE

MAELRLKGSS NTTECVPVPT SEHVAEIVGR QGCKIKALRA KTNTYIKTPV RGEEPVFMVT GRREDVATAR REIISAAEHF SMIRASRNKS
GAAFCVAPAL PGQVTIRVRV PYRVVGLVVG PKGATIKRIQ QQTNTVIITP SRDRDPVFEI TGAPGNVERA REEIETHIAV RIGKILEYNN
ENDFLAGSPD AAIDSRYSDA WRVHQPGCKP LSTFRQMSLG CIGECGVDSG FEAPRLGEQG GDFGYGGYLE PGYGVGKQDV YYGVAETSPP
LWAGQENATP TSVLFSSASS SSSSSAKARA GPPGAHRSPA TSAGPELAGL PRRPPGEPLQ GFSKLSGGGL RSPGGGREGM VCFESEVTAA
LVFCGHNLFC MECAVRICER TDPECPVCHI TAAQAIRIFS

SEQUENCE LISTING

<160> NUMBER OF SEQ ID NOS: 218

<210> SEQ ID NO 1
<211> LENGTH: 3846
<212> TYPE: DNA
<213> ORGANISM: Homo sapiens

<400> SEQUENCE: 1

| | | | | | |
|---|---|---|---|---|---|
| atggtccgga | aaaagaaccc | ccctctgaga | aacgttgcaa | gtgaaggcga | gggccagatc | 60 |
| ctggagccta | taggtacaga | aagcaaggta | tctggaaaga | acaaagaatt | ctctgcagat | 120 |
| cagatgtcag | aaaatacgga | tcagagtgat | gctgcagaac | taaatcataa | ggaggaacat | 180 |

```
agcttgcatg ttcaagatcc atcttctagc agtaagaagg acttgaaaag cgcagttctg      240
agtgagaagg ctggcttcaa ttatgaaagc cccagtaagg gaggaaactt tccctccttt      300
ccgcatgatg aggtgacaga cagaaatatg ttggctttct catttccagc tgctggggga      360
gtctgtgagc ccttgaagtc tccgcaaaga gcagaggcag atgaccctca agatatggcc      420
tgcacccect cagggactc actggagaca aggaagatc agaagatgtc accaaaggct        480
acagaggaaa cagggcaagc acagagtggt caagccaatt gtcaaggttt gagcccagtt      540
tcagtggcct caaaaaaccc acaagtgcct tcagatgggg gtgtaagact gaataaatcc      600
aaaactgact tactggtgaa tgacaaccca gacccgcac ctctgtctcc agagcttcag       660
gactttaaat gcaatatctg tggatatggt tactacggca acgacccac agatctgatt       720
aagcacttcc gaaagtatca cttaggactg cataaccgca ccaggcaaga tgctgagctg      780
gacagcaaaa tcttggccct tcataacatg gtgcagttca gccattccaa agacttccag      840
aaggtcaacc gttctgtgtt ttctggtgtg ctgcaggaca tcaattcttc aaggcctgtt      900
ttactaaatg ggacctatga tgtgcaggtg acttcaggtg gaacattcat tggcattgga      960
cggaaaacac cagattgcca agggaacacc aagtatttcc gctgtaaatt ctgcaatttc     1020
acttatatgg gcaactcatc caccgaatta gaacaacatt ttcttcagac tcacccaaac     1080
aaaataaaag cttctctccc ctcctctgag gttgcaaaac cttcagagaa aaactctaac     1140
aagtccatcc ctgcacttca atccagtgat tctggagact tgggaaaatg gcaggacaag     1200
ataacagtca aagcaggaga tgacactcct gttgggtact cagtgcccat aaagcccctc     1260
gattcctcta gacaaaatgg tacagaggcc accagttact actggtgtaa attttgtagt     1320
ttcagctgtg agtcatctag ctcacttaaa ctgctagaac attatggcaa gcagcacgga     1380
gcagtgcagt caggcggcct taatccagag ttaaatgata agctttccag gggctctgtc     1440
attaatcaga atgatctagc caaaagttca gaaggagaga caatgaccaa gacagacaag     1500
agctcgagtg gggctaaaaa gaaggacttc tccagcaagg gagccgagga taatatggta     1560
acgagctata attgtcagtt ctgtgacttc cgatattcca aaagccatgg ccctgatgta     1620
attgtagtgg ggccacttct ccgtcattat caacagctcc ataacattca caagtgtacc     1680
attaaacact gtccattctg tcccagagga ctttgcagcc cagaaaagca ccttggagaa     1740
attacttatc cgtttgcttg tagaaaaagt aattgttccc actgtgcact cttgcttctg     1800
cacttgtctc ctggggcggc tggaagctcg cgagtcaaac atcagtgcca tcagtgttca     1860
ttcaccaccc ctgacgtaga tgtactcctc tttcactatg aaagtgtgca tgagtcccaa     1920
gcatcggatg tcaaacaaga agcaaatcac ctgcaaggat cggatgggca gcagtctgtc     1980
aaggaaagca aagaacactc atgtaccaaa tgtgatttta ttacccaagt ggaagaagag     2040
atttcccgac actacaggag agcacacagc tgctacaaat gccgtcagtg cagtttttaca     2100
gctgccgata ctcagtcact actggagcac ttcaacactg ttcactgcca ggaacaggac     2160
atcactacag ccaacggcga agaggacggt catgccatat ccaccatcaa agaggagccc     2220
aaaattgact tcagggtcta caatctgcta actccagact ctaaaatggg agagccagtt     2280
tctgagagtg tggtgaagag agaagctg gaagagaagg acgggctcaa agagaaagtt      2340
tggaccgaga gttccagtga tgaccttcgc aatgtgactt ggagagggggc agacatcctg     2400
cgggggagtc cgtcatacac ccaagcaagc ctggggctgc tgacgcctgt gtctggcacc     2460
caagagcaga caaagactct aagggatagt cccaatgtgg aggccgccca tctggcgcga     2520
cctatttatg gcttggctgt ggaaaccaag ggattcctgc aggggcgcc agctggcgga     2580
```

-continued

```
gagaagtctg gggccctccc ccagcagtat cctgcatcgg gagaaaacaa gtccaaggat    2640
gaatcccagt ccctgttacg gaggcgtaga ggctccggtg ttttttgtgc caattgcctg    2700
accacaaaga cctctctctg gcgaaagaat gcaaatggcg gatatgtatg caacgcgtgt    2760
ggcctctacc agaagcttca ctcgactccc aggccttttaa acatcattaa acaaaacaac    2820
ggtgagcaga ttattaggag gagaacaaga aagcgcctta acccagaggc acttcaggct    2880
gagcagctca acaaacagca gaggggcagc aatgaggagc aagtcaatgg aagcccgtta    2940
gagaggaggt cagaagatca tctaactgaa agtcaccaga gagaaattcc actccccagc    3000
ctaagtaaat acgaagccca gggttcattg actaaaagcc attctgctca gcagccagtc    3060
ctggtcagcc aaactctgga tattcacaaa aggatgcaac ctttgcacat tcagataaaa    3120
agtcctcagg aaagtactgg agatccagga aatagttcat ccgtatctga agggaaagga    3180
agttctgaga gaggcagtcc tatagaaaag tacatgagac ctgcgaaaca cccaaattat    3240
tcaccaccag gcagccctat tgaaaagtac cagtacccac ttttttggact tccctttgta    3300 cataatgact tccagagtga agctgattgg ctgcggttct ggagtaaata taagctctcc    3360
gttcctggga atccgcacta cttgagtcac gtgcctggcc taccaaatcc ttgccaaaac    3420
tatgtgcctt atcccacctt caatctgcct cctcattttt cagctgttgg atcagacaat    3480
gacattcctc tagatttggc gatcaagcat tccagacctg gccaactgc aaacggtgcc    3540 tccaaggaga aaacgaaggc accaccaaat gtaaaaaatg aaggtcccctt gaatgtagta    3600 aaaacagaga aagttgatag aagtactcaa gatgaacttt caacaaaatg tgtgcactgt    3660
ggcattgtct ttctggatga agtgatgtat gctttgcata tgagttgcca tggtgacagt    3720
ggacctttcc agtgcagcat atgccagcat ctttgcacgg acaaatatga cttcacaaca    3780
catatccaga ggggcctgca taggaacaat gcacaagtgg aaaaaaatgg aaaacctaaa    3840
gagtaa                                                              3846
```

<210> SEQ ID NO 2
<211> LENGTH: 1281
<212> TYPE: PRT
<213> ORGANISM: Homo sapiens

<400> SEQUENCE: 2

```
Met Val Arg Lys Lys Asn Pro Pro Leu Arg Asn Val Ala Ser Glu Gly
  1               5                  10                  15

Glu Gly Gln Ile Leu Glu Pro Ile Gly Thr Glu Ser Lys Val Ser Gly
             20                  25                  30

Lys Asn Lys Glu Phe Ser Ala Asp Gln Met Ser Glu Asn Thr Asp Gln
         35                  40                  45

Ser Asp Ala Ala Glu Leu Asn His Lys Glu Glu His Ser Leu His Val
     50                  55                  60

Gln Asp Pro Ser Ser Ser Lys Lys Asp Leu Lys Ser Ala Val Leu
 65                  70                  75                  80

Ser Glu Lys Ala Gly Phe Asn Tyr Glu Ser Pro Ser Lys Gly Gly Asn
                 85                  90                  95

Phe Pro Ser Phe Pro His Asp Glu Val Thr Asp Arg Asn Met Leu Ala
            100                 105                 110

Phe Ser Phe Pro Ala Ala Gly Gly Val Cys Glu Pro Leu Lys Ser Pro
        115                 120                 125

Gln Arg Ala Glu Ala Asp Asp Pro Gln Asp Met Ala Cys Thr Pro Ser
    130                 135                 140
```

-continued

```
Gly Asp Ser Leu Glu Thr Lys Glu Asp Gln Lys Met Ser Pro Lys Ala
145                 150                 155                 160

Thr Glu Glu Thr Gly Gln Ala Gln Ser Gly Gln Ala Asn Cys Gln Gly
                165                 170                 175

Leu Ser Pro Val Ser Val Ala Ser Lys Asn Pro Gln Val Pro Ser Asp
            180                 185                 190

Gly Gly Val Arg Leu Asn Lys Ser Lys Thr Asp Leu Leu Val Asn Asp
        195                 200                 205

Asn Pro Asp Pro Ala Pro Leu Ser Pro Glu Leu Gln Asp Phe Lys Cys
210                 215                 220

Asn Ile Cys Gly Tyr Gly Tyr Gly Asn Asp Pro Thr Asp Leu Ile
225                 230                 235                 240

Lys His Phe Arg Lys Tyr His Leu Gly Leu His Asn Arg Thr Arg Gln
                245                 250                 255

Asp Ala Glu Leu Asp Ser Lys Ile Leu Ala Leu His Asn Met Val Gln
            260                 265                 270

Phe Ser His Ser Lys Asp Phe Gln Lys Val Asn Arg Ser Val Phe Ser
        275                 280                 285

Gly Val Leu Gln Asp Ile Asn Ser Ser Arg Pro Val Leu Leu Asn Gly
        290                 295                 300

Thr Tyr Asp Val Gln Val Thr Ser Gly Gly Thr Phe Ile Gly Ile Gly
305                 310                 315                 320

Arg Lys Thr Pro Asp Cys Gln Gly Asn Thr Lys Tyr Phe Arg Cys Lys
                325                 330                 335

Phe Cys Asn Phe Thr Tyr Met Gly Asn Ser Ser Thr Glu Leu Glu Gln
            340                 345                 350

His Phe Leu Gln Thr His Pro Asn Lys Ile Lys Ala Ser Leu Pro Ser
        355                 360                 365

Ser Glu Val Ala Lys Pro Ser Glu Lys Asn Ser Asn Lys Ser Ile Pro
        370                 375                 380

Ala Leu Gln Ser Ser Asp Ser Gly Asp Leu Gly Lys Trp Gln Asp Lys
385                 390                 395                 400

Ile Thr Val Lys Ala Gly Asp Asp Thr Pro Val Gly Tyr Ser Val Pro
                405                 410                 415

Ile Lys Pro Leu Asp Ser Ser Arg Gln Asn Gly Thr Glu Ala Thr Ser
            420                 425                 430

Tyr Tyr Trp Cys Lys Phe Cys Ser Phe Ser Cys Glu Ser Ser Ser Ser
        435                 440                 445

Leu Lys Leu Leu Glu His Tyr Gly Lys Gln His Gly Ala Val Gln Ser
        450                 455                 460

Gly Gly Leu Asn Pro Glu Leu Asn Asp Lys Leu Ser Arg Gly Ser Val
465                 470                 475                 480

Ile Asn Gln Asn Asp Leu Ala Lys Ser Ser Glu Gly Glu Thr Met Thr
                485                 490                 495

Lys Thr Asp Lys Ser Ser Gly Ala Lys Lys Asp Phe Ser Ser
            500                 505                 510

Lys Gly Ala Glu Asp Asn Met Val Thr Ser Tyr Asn Cys Gln Phe Cys
        515                 520                 525

Asp Phe Arg Tyr Ser Lys Ser His Gly Pro Asp Val Ile Val Val Gly
        530                 535                 540

Pro Leu Leu Arg His Tyr Gln Gln Leu His Asn Ile His Lys Cys Thr
545                 550                 555                 560
```

-continued

```
Ile Lys His Cys Pro Phe Cys Pro Arg Gly Leu Cys Ser Pro Glu Lys
            565                 570                 575

His Leu Gly Glu Ile Thr Tyr Pro Phe Ala Cys Arg Lys Ser Asn Cys
        580                 585                 590

Ser His Cys Ala Leu Leu Leu His Leu Ser Pro Gly Ala Ala Gly
    595                 600                 605

Ser Ser Arg Val Lys His Gln Cys His Gln Cys Ser Phe Thr Thr Pro
610                 615                 620

Asp Val Asp Val Leu Leu Phe His Tyr Glu Ser Val His Glu Ser Gln
625                 630                 635                 640

Ala Ser Asp Val Lys Gln Glu Ala Asn His Leu Gln Gly Ser Asp Gly
                645                 650                 655

Gln Gln Ser Val Lys Glu Ser Lys Glu His Ser Cys Thr Lys Cys Asp
            660                 665                 670

Phe Ile Thr Gln Val Glu Glu Ile Ser Arg His Tyr Arg Arg Ala
        675                 680                 685

His Ser Cys Tyr Lys Cys Arg Gln Cys Ser Phe Thr Ala Ala Asp Thr
    690                 695                 700

Gln Ser Leu Leu Glu His Phe Asn Thr Val His Cys Gln Glu Gln Asp
705                 710                 715                 720

Ile Thr Thr Ala Asn Gly Glu Glu Asp Gly His Ala Ile Ser Thr Ile
                725                 730                 735

Lys Glu Glu Pro Lys Ile Asp Phe Arg Val Tyr Asn Leu Leu Thr Pro
            740                 745                 750

Asp Ser Lys Met Gly Glu Pro Val Ser Glu Ser Val Val Lys Arg Glu
        755                 760                 765

Lys Leu Glu Glu Lys Asp Gly Leu Lys Glu Lys Val Trp Thr Glu Ser
    770                 775                 780

Ser Ser Asp Asp Leu Arg Asn Val Thr Trp Arg Gly Ala Asp Ile Leu
785                 790                 795                 800

Arg Gly Ser Pro Ser Tyr Thr Gln Ala Ser Leu Gly Leu Leu Thr Pro
                805                 810                 815

Val Ser Gly Thr Gln Glu Gln Thr Lys Thr Leu Arg Asp Ser Pro Asn
            820                 825                 830

Val Glu Ala Ala His Leu Ala Arg Pro Ile Tyr Gly Leu Ala Val Glu
        835                 840                 845

Thr Lys Gly Phe Leu Gln Gly Ala Pro Ala Gly Glu Lys Ser Gly
    850                 855                 860

Ala Leu Pro Gln Gln Tyr Pro Ala Ser Gly Glu Asn Lys Ser Lys Asp
865                 870                 875                 880

Glu Ser Gln Ser Leu Leu Arg Arg Arg Gly Ser Gly Val Phe Cys
                885                 890                 895

Ala Asn Cys Leu Thr Thr Lys Thr Ser Leu Trp Arg Lys Asn Ala Asn
            900                 905                 910

Gly Gly Tyr Val Cys Asn Ala Cys Gly Leu Tyr Gln Lys Leu His Ser
        915                 920                 925

Thr Pro Arg Pro Leu Asn Ile Ile Lys Gln Asn Gly Glu Gln Ile
    930                 935                 940

Ile Arg Arg Arg Thr Arg Lys Arg Leu Asn Pro Glu Ala Leu Gln Ala
945                 950                 955                 960

Glu Gln Leu Asn Lys Gln Gln Arg Gly Ser Asn Glu Glu Gln Val Asn
                965                 970                 975

Gly Ser Pro Leu Glu Arg Arg Ser Glu Asp His Leu Thr Glu Ser His
```

```
                980             985             990
Gln Arg Glu Ile Pro Leu Pro Ser  Leu Ser Lys Tyr  Glu Ala Gln Gly
         995             1000            1005
Ser Leu Thr Lys Ser His Ser Ala  Gln Gln Pro Val  Leu Val Ser
         1010            1015            1020
Gln Thr Leu Asp Ile His Lys Arg  Met Gln Pro Leu  His Ile Gln
         1025            1030            1035
Ile Lys Ser Pro Gln Glu Ser Thr  Gly Asp Pro Gly  Asn Ser Ser
         1040            1045            1050
Ser Val Ser Glu Gly Lys Gly Ser  Ser Glu Arg Gly  Ser Pro Ile
         1055            1060            1065
Glu Lys Tyr Met Arg Pro Ala Lys  His Pro Asn Tyr  Ser Pro Pro
         1070            1075            1080
Gly Ser Pro Ile Glu Lys Tyr Gln  Tyr Pro Leu Phe  Gly Leu Pro
         1085            1090            1095
Phe Val His Asn Asp Phe Gln Ser  Glu Ala Asp Trp  Leu Arg Phe
         1100            1105            1110
Trp Ser Lys Tyr Lys Leu Ser Val  Pro Gly Asn Pro  His Tyr Leu
         1115            1120            1125
Ser His Val Pro Gly Leu Pro Asn  Pro Cys Gln Asn  Tyr Val Pro
         1130            1135            1140
Tyr Pro Thr Phe Asn Leu Pro Pro  His Phe Ser Ala  Val Gly Ser
         1145            1150            1155
Asp Asn Asp Ile Pro Leu Asp Leu  Ala Ile Lys His  Ser Arg Pro
         1160            1165            1170
Gly Pro Thr Ala Asn Gly Ala Ser  Lys Glu Lys Thr  Lys Ala Pro
         1175            1180            1185
Pro Asn Val Lys Asn Glu Gly Pro  Leu Asn Val Val  Lys Thr Glu
         1190            1195            1200
Lys Val Asp Arg Ser Thr Gln Asp  Glu Leu Ser Thr  Lys Cys Val
         1205            1210            1215
His Cys Gly Ile Val Phe Leu Asp  Glu Val Met Tyr  Ala Leu His
         1220            1225            1230
Met Ser Cys His Gly Asp Ser Gly  Pro Phe Gln Cys  Ser Ile Cys
         1235            1240            1245
Gln His Leu Cys Thr Asp Lys Tyr  Asp Phe Thr Thr  His Ile Gln
         1250            1255            1260
Arg Gly Leu His Arg Asn Asn Ala  Gln Val Glu Lys  Asn Gly Lys
         1265            1270            1275
Pro Lys Glu
         1280

<210> SEQ ID NO 3
<211> LENGTH: 1203
<212> TYPE: DNA
<213> ORGANISM: Homo sapiens

<400> SEQUENCE: 3
atggccgagc tgcgcctgaa gggcagcagc aacaccacgg agtgtgttcc cgtgcccacc    60
tccgagcacg tggccgagat cgtgggcagg caaggctgca agattaaggc cttgagggcc   120
aagaccaaca cctacatcaa gaccggtg   agggggcgagg aaccagtgtt catggtgaca   180
gggcgacggg aggacgtggc cacagcccgg cgggaaatca tctcagcagc ggagcacttc   240
tccatgatcc gtgcctcccg caacaagtca ggcgccgcct ttggtgtggc tcctgctctg   300
```

-continued

```
cccggccagg tgaccatccg tgtgcgggtg ccctaccgcg tggtggggct ggtggtgggc    360
cccaaagggg caaccatcaa gcgcatccag cagcaaacca acacatacat tatcacacca    420
agccgtgacc gcgaccccgt gttcgagatc acgggtgccc caggcaacgt ggagcgtgcg    480
cgcgaggaga tcgagacgca catcgcggtg cgcactggca agatcctcga gtacaacaat    540
gaaaacgact tcctggcggg gagccccgac gcagcaatcg atagccgcta ctccgacgcc    600
tggcgggtgc accagcccgg ctgcaagccc ctctccacct tccggcagaa cagcctgggc    660
tgcatcggcg agtgcggagt ggactctggc tttgaggccc cacgcctggg tgagcagggc    720
ggggactttg gctacggcgg gtacctcttt ccgggctatg gcgtgggcaa gcaggatgtg    780
tactacggcg tggccgagac tagccccccg ctgtgggcgg gccaggagaa cgccacgccc    840
acctccgtgc tcttctcctc tgcctcctcc tcctcctcct cttccgccaa ggcccgcgct    900 gggccccgg gcgcacaccg ctcccctgcc acttccgcgg gacccgagct ggccggactc    960
ccgaggcgcc cccggggaga gccgctccag ggcttctcta aacttggtgg gggcggcctg   1020
cggagccccg gcggcgggcg ggattgcatg gtctgctttg agagcgaagt gactgccgcc   1080
cttgtgccct gcggacacaa cctgttctgc atggagtgtg cagtacgcat ctgcgagagg   1140
acggacccag agtgtcccgt ctgccacatc acagccgcgc aagccatccg aatattctcc   1200
taa                                                                  1203
```

<210> SEQ ID NO 4
<211> LENGTH: 400
<212> TYPE: PRT
<213> ORGANISM: Homo sapiens

<400> SEQUENCE: 4

```
Met Ala Glu Leu Arg Leu Lys Gly Ser Ser Asn Thr Thr Glu Cys Val
1               5                   10                  15

Pro Val Pro Thr Ser Glu His Val Ala Glu Ile Val Gly Arg Gln Gly
                20                  25                  30

Cys Lys Ile Lys Ala Leu Arg Ala Lys Thr Asn Thr Tyr Ile Lys Thr
            35                  40                  45

Pro Val Arg Gly Glu Glu Pro Val Phe Met Val Thr Gly Arg Arg Glu
        50                  55                  60

Asp Val Ala Thr Ala Arg Arg Glu Ile Ile Ser Ala Ala Glu His Phe
65                  70                  75                  80

Ser Met Ile Arg Ala Ser Arg Asn Lys Ser Gly Ala Ala Phe Gly Val
                85                  90                  95

Ala Pro Ala Leu Pro Gly Gln Val Thr Ile Arg Val Arg Val Pro Tyr
            100                 105                 110

Arg Val Val Gly Leu Val Val Gly Pro Lys Gly Ala Thr Ile Lys Arg
        115                 120                 125

Ile Gln Gln Gln Thr Asn Thr Tyr Ile Ile Thr Pro Ser Arg Asp Arg
    130                 135                 140

Asp Pro Val Phe Glu Ile Thr Gly Ala Pro Gly Asn Val Glu Arg Ala
145                 150                 155                 160

Arg Glu Glu Ile Glu Thr His Ile Ala Val Arg Thr Gly Lys Ile Leu
                165                 170                 175

Glu Tyr Asn Asn Glu Asn Asp Phe Leu Ala Gly Ser Pro Asp Ala Ala
            180                 185                 190

Ile Asp Ser Arg Tyr Ser Asp Ala Trp Arg Val His Gln Pro Gly Cys
        195                 200                 205
```

-continued

```
Lys Pro Leu Ser Thr Phe Arg Gln Asn Ser Leu Gly Cys Ile Gly Glu
    210                 215                 220
Cys Gly Val Asp Ser Gly Phe Glu Ala Pro Arg Leu Gly Glu Gln Gly
225                 230                 235                 240
Gly Asp Phe Gly Tyr Gly Gly Tyr Leu Phe Pro Gly Tyr Gly Val Gly
                245                 250                 255
Lys Gln Asp Val Tyr Tyr Gly Val Ala Glu Thr Ser Pro Pro Leu Trp
            260                 265                 270
Ala Gly Gln Glu Asn Ala Thr Pro Thr Ser Val Leu Phe Ser Ser Ala
        275                 280                 285
Ser Ser Ser Ser Ser Ser Ala Lys Ala Arg Ala Gly Pro Pro Gly
    290                 295                 300
Ala His Arg Ser Pro Ala Thr Ser Ala Gly Pro Glu Leu Ala Gly Leu
305                 310                 315                 320
Pro Arg Arg Pro Pro Gly Glu Pro Leu Gln Gly Phe Ser Lys Leu Gly
                325                 330                 335
Gly Gly Gly Leu Arg Ser Pro Gly Gly Arg Asp Cys Met Val Cys
            340                 345                 350
Phe Glu Ser Glu Val Thr Ala Ala Leu Val Pro Cys Gly His Asn Leu
        355                 360                 365
Phe Cys Met Glu Cys Ala Val Arg Ile Cys Glu Arg Thr Asp Pro Glu
    370                 375                 380
Cys Pro Val Cys His Ile Thr Ala Ala Gln Ala Ile Arg Ile Phe Ser
385                 390                 395                 400

<210> SEQ ID NO 5
<211> LENGTH: 22
<212> TYPE: PRT
<213> ORGANISM: Artificial
<220> FEATURE:
<223> OTHER INFORMATION: CLP 2589

<400> SEQUENCE: 5

Met Val Arg Lys Lys Asn Pro Pro Leu Arg Asn Val Ala Ser Glu Gly
1               5                   10                  15
Glu Gly Gln Ile Leu Glu
            20

<210> SEQ ID NO 6
<211> LENGTH: 22
<212> TYPE: PRT
<213> ORGANISM: Artificial
<220> FEATURE:
<223> OTHER INFORMATION: CLP 2590

<400> SEQUENCE: 6

Ser Pro Lys Ala Thr Glu Glu Thr Gly Gln Ala Gln Ser Gly Gln Ala
1               5                   10                  15
Asn Cys Gln Gly Leu Ser
            20

<210> SEQ ID NO 7
<211> LENGTH: 22
<212> TYPE: PRT
<213> ORGANISM: Artificial
<220> FEATURE:
<223> OTHER INFORMATION: CLP 2591

<400> SEQUENCE: 7
```

```
Val Ala Lys Pro Ser Glu Lys Asn Ser Asn Lys Ser Ile Pro Ala Leu
1               5                   10                  15

Gln Ser Ser Asp Ser Gly
            20

<210> SEQ ID NO 8
<211> LENGTH: 22
<212> TYPE: PRT
<213> ORGANISM: Artificial
<220> FEATURE:
<223> OTHER INFORMATION: CLP 2592

<400> SEQUENCE: 8

Asn His Leu Gln Gly Ser Asp Gly Gln Gln Ser Val Lys Glu Ser Lys
1               5                   10                  15

Glu His Ser Cys Thr Lys
            20

<210> SEQ ID NO 9
<211> LENGTH: 22
<212> TYPE: PRT
<213> ORGANISM: Artificial
<220> FEATURE:
<223> OTHER INFORMATION: CLP 2593

<400> SEQUENCE: 9

Asn Gly Glu Gln Ile Ile Arg Arg Arg Thr Arg Lys Arg Leu Asn Pro
1               5                   10                  15

Glu Ala Leu Gln Ala Glu
            20

<210> SEQ ID NO 10
<211> LENGTH: 23
<212> TYPE: PRT
<213> ORGANISM: Artificial
<220> FEATURE:
<223> OTHER INFORMATION: CLP 2594

<400> SEQUENCE: 10

Ala Asn Gly Ala Ser Lys Glu Lys Thr Lys Ala Pro Pro Asn Val Lys
1               5                   10                  15

Asn Glu Gly Pro Leu Asn Val
            20

<210> SEQ ID NO 11
<211> LENGTH: 32
<212> TYPE: DNA
<213> ORGANISM: Artificial
<220> FEATURE:
<223> OTHER INFORMATION: Primer 7717

<400> SEQUENCE: 11
cgggatccac catggtccgg aaaaagaacc cc                              32

<210> SEQ ID NO 12
<211> LENGTH: 35
<212> TYPE: DNA
<213> ORGANISM: Artificial
<220> FEATURE:
<223> OTHER INFORMATION: Primer 7723

<400> SEQUENCE: 12
cgggatccct ctttaggttt tccattttt tccac                            35
```

```
<210> SEQ ID NO 13
<211> LENGTH: 9
<212> TYPE: PRT
<213> ORGANISM: Artificial
<220> FEATURE:
<223> OTHER INFORMATION: CLP-2421

<400> SEQUENCE: 13

Met Val Arg Lys Lys Asn Pro Pro Leu
1               5

<210> SEQ ID NO 14
<211> LENGTH: 9
<212> TYPE: PRT
<213> ORGANISM: Artificial
<220> FEATURE:
<223> OTHER INFORMATION: CLP-2422

<400> SEQUENCE: 14

Lys Lys Asn Pro Pro Leu Arg Asn Val
1               5

<210> SEQ ID NO 15
<211> LENGTH: 9
<212> TYPE: PRT
<213> ORGANISM: Artificial
<220> FEATURE:
<223> OTHER INFORMATION: CLP-2423

<400> SEQUENCE: 15

Val Ala Ser Glu Gly Glu Gly Gln Ile
1               5

<210> SEQ ID NO 16
<211> LENGTH: 9
<212> TYPE: PRT
<213> ORGANISM: Artificial
<220> FEATURE:
<223> OTHER INFORMATION: CLP-2424

<400> SEQUENCE: 16

Gln Ile Leu Glu Pro Ile Gly Thr Glu
1               5

<210> SEQ ID NO 17
<211> LENGTH: 9
<212> TYPE: PRT
<213> ORGANISM: Artificial
<220> FEATURE:
<223> OTHER INFORMATION: CLP-2425

<400> SEQUENCE: 17

Arg Asn Met Leu Ala Phe Ser Phe Pro
1               5

<210> SEQ ID NO 18
<211> LENGTH: 9
<212> TYPE: PRT
<213> ORGANISM: Artificial
<220> FEATURE:
<223> OTHER INFORMATION: CLP-2426

<400> SEQUENCE: 18

Asn Met Leu Ala Phe Ser Phe Pro Ala
1               5

<210> SEQ ID NO 19
```

```
<211> LENGTH: 9
<212> TYPE: PRT
<213> ORGANISM: Artificial
<220> FEATURE:
<223> OTHER INFORMATION: CLP-2427

<400> SEQUENCE: 19

Met Leu Ala Phe Ser Phe Pro Ala Ala
1               5

<210> SEQ ID NO 20
<211> LENGTH: 9
<212> TYPE: PRT
<213> ORGANISM: Artificial
<220> FEATURE:
<223> OTHER INFORMATION: CLP-2428

<400> SEQUENCE: 20

Phe Ser Phe Pro Ala Ala Gly Gly Val
1               5

<210> SEQ ID NO 21
<211> LENGTH: 9
<212> TYPE: PRT
<213> ORGANISM: Artificial
<220> FEATURE:
<223> OTHER INFORMATION: CLP-2429

<400> SEQUENCE: 21

Ala Ala Gly Gly Val Cys Glu Pro Leu
1               5

<210> SEQ ID NO 22
<211> LENGTH: 9
<212> TYPE: PRT
<213> ORGANISM: Artificial
<220> FEATURE:
<223> OTHER INFORMATION: CLP-2430

<400> SEQUENCE: 22

Ser Gly Gln Ala Asn Cys Gln Gly Leu
1               5

<210> SEQ ID NO 23
<211> LENGTH: 9
<212> TYPE: PRT
<213> ORGANISM: Artificial
<220> FEATURE:
<223> OTHER INFORMATION: CLP-2431

<400> SEQUENCE: 23

Ala Asn Cys Gln Gly Leu Ser Pro Val
1               5

<210> SEQ ID NO 24
<211> LENGTH: 9
<212> TYPE: PRT
<213> ORGANISM: Artificial
<220> FEATURE:
<223> OTHER INFORMATION: CLP-2432

<400> SEQUENCE: 24

Gly Leu Ser Pro Val Ser Val Ala Ser
1               5

<210> SEQ ID NO 25
<211> LENGTH: 9
```

```
<212> TYPE: PRT
<213> ORGANISM: Artificial
<220> FEATURE:
<223> OTHER INFORMATION: CLP-2433

<400> SEQUENCE: 25

Ser Val Ala Ser Lys Asn Pro Gln Val
1               5

<210> SEQ ID NO 26
<211> LENGTH: 9
<212> TYPE: PRT
<213> ORGANISM: Artificial
<220> FEATURE:
<223> OTHER INFORMATION: CLP-2434

<400> SEQUENCE: 26

Arg Leu Asn Lys Ser Lys Thr Asp Leu
1               5

<210> SEQ ID NO 27
<211> LENGTH: 9
<212> TYPE: PRT
<213> ORGANISM: Artificial
<220> FEATURE:
<223> OTHER INFORMATION: CLP-2435

<400> SEQUENCE: 27

Asn Asp Asn Pro Asp Pro Ala Pro Leu
1               5

<210> SEQ ID NO 28
<211> LENGTH: 9
<212> TYPE: PRT
<213> ORGANISM: Artificial
<220> FEATURE:
<223> OTHER INFORMATION: CLP-2436

<400> SEQUENCE: 28

Asp Pro Ala Pro Leu Ser Pro Glu Leu
1               5

<210> SEQ ID NO 29
<211> LENGTH: 9
<212> TYPE: PRT
<213> ORGANISM: Artificial
<220> FEATURE:
<223> OTHER INFORMATION: CLP-2437

<400> SEQUENCE: 29

Glu Leu Gln Asp Phe Lys Cys Asn Ile
1               5

<210> SEQ ID NO 30
<211> LENGTH: 9
<212> TYPE: PRT
<213> ORGANISM: Artificial
<220> FEATURE:
<223> OTHER INFORMATION: CLP-2438

<400> SEQUENCE: 30

Gly Leu His Asn Arg Thr Arg Gln Asp
1               5

<210> SEQ ID NO 31
<211> LENGTH: 9
<212> TYPE: PRT
```

```
<213> ORGANISM: Artificial
<220> FEATURE:
<223> OTHER INFORMATION: CLP-2439

<400> SEQUENCE: 31

Glu Leu Asp Ser Lys Ile Leu Ala Leu
1               5

<210> SEQ ID NO 32
<211> LENGTH: 9
<212> TYPE: PRT
<213> ORGANISM: Artificial
<220> FEATURE:
<223> OTHER INFORMATION: CLP-2440

<400> SEQUENCE: 32

Lys Ile Leu Ala Leu His Asn Met Val
1               5

<210> SEQ ID NO 33
<211> LENGTH: 9
<212> TYPE: PRT
<213> ORGANISM: Artificial
<220> FEATURE:
<223> OTHER INFORMATION: CLP-2441

<400> SEQUENCE: 33

Ala Leu His Asn Met Val Gln Phe Ser
1               5

<210> SEQ ID NO 34
<211> LENGTH: 9
<212> TYPE: PRT
<213> ORGANISM: Artificial
<220> FEATURE:
<223> OTHER INFORMATION: CLP-2442

<400> SEQUENCE: 34

Val Asn Arg Ser Val Phe Ser Gly Val
1               5

<210> SEQ ID NO 35
<211> LENGTH: 9
<212> TYPE: PRT
<213> ORGANISM: Artificial
<220> FEATURE:
<223> OTHER INFORMATION: CLP-2443

<400> SEQUENCE: 35

Phe Ser Gly Val Leu Gln Asp Ile Asn
1               5

<210> SEQ ID NO 36
<211> LENGTH: 9
<212> TYPE: PRT
<213> ORGANISM: Artificial
<220> FEATURE:
<223> OTHER INFORMATION: CLP-2444

<400> SEQUENCE: 36

Asp Ile Asn Ser Ser Arg Pro Val Leu
1               5

<210> SEQ ID NO 37
<211> LENGTH: 9
<212> TYPE: PRT
<213> ORGANISM: Artificial
```

```
<220> FEATURE:
<223> OTHER INFORMATION: CLP-2445

<400> SEQUENCE: 37

Val Leu Leu Asn Gly Thr Tyr Asp Val
1               5

<210> SEQ ID NO 38
<211> LENGTH: 9
<212> TYPE: PRT
<213> ORGANISM: Artificial
<220> FEATURE:
<223> OTHER INFORMATION: CLP-2446

<400> SEQUENCE: 38

Phe Cys Asn Phe Thr Tyr Met Gly Asn
1               5

<210> SEQ ID NO 39
<211> LENGTH: 9
<212> TYPE: PRT
<213> ORGANISM: Artificial
<220> FEATURE:
<223> OTHER INFORMATION: CLP-2447

<400> SEQUENCE: 39

Tyr Met Gly Asn Ser Ser Thr Glu Leu
1               5

<210> SEQ ID NO 40
<211> LENGTH: 9
<212> TYPE: PRT
<213> ORGANISM: Artificial
<220> FEATURE:
<223> OTHER INFORMATION: CLP-2448

<400> SEQUENCE: 40

Phe Leu Gln Thr His Pro Asn Lys Ile
1               5

<210> SEQ ID NO 41
<211> LENGTH: 9
<212> TYPE: PRT
<213> ORGANISM: Artificial
<220> FEATURE:
<223> OTHER INFORMATION: CLP-2449

<400> SEQUENCE: 41

Lys Ala Ser Leu Pro Ser Ser Glu Val
1               5

<210> SEQ ID NO 42
<211> LENGTH: 9
<212> TYPE: PRT
<213> ORGANISM: Artificial
<220> FEATURE:
<223> OTHER INFORMATION: CLP-2450

<400> SEQUENCE: 42

Asp Leu Gly Lys Trp Gln Asp Lys Ile
1               5

<210> SEQ ID NO 43
<211> LENGTH: 9
<212> TYPE: PRT
<213> ORGANISM: Artificial
<220> FEATURE:
```

```
<223> OTHER INFORMATION: CLP-2451

<400> SEQUENCE: 43

Val Lys Ala Gly Asp Asp Thr Pro Val
1               5

<210> SEQ ID NO 44
<211> LENGTH: 9
<212> TYPE: PRT
<213> ORGANISM: Artificial
<220> FEATURE:
<223> OTHER INFORMATION: CLP-2452

<400> SEQUENCE: 44

Phe Ser Cys Glu Ser Ser Ser Ser Leu
1               5

<210> SEQ ID NO 45
<211> LENGTH: 9
<212> TYPE: PRT
<213> ORGANISM: Artificial
<220> FEATURE:
<223> OTHER INFORMATION: CLP-2453

<400> SEQUENCE: 45

Lys Leu Leu Glu His Tyr Gly Lys Gln
1               5

<210> SEQ ID NO 46
<211> LENGTH: 9
<212> TYPE: PRT
<213> ORGANISM: Artificial
<220> FEATURE:
<223> OTHER INFORMATION: CLP-2454

<400> SEQUENCE: 46

Gly Leu Asn Pro Glu Leu Asn Asp Lys
1               5

<210> SEQ ID NO 47
<211> LENGTH: 9
<212> TYPE: PRT
<213> ORGANISM: Artificial
<220> FEATURE:
<223> OTHER INFORMATION: CLP-2455

<400> SEQUENCE: 47

Gly Ser Val Ile Asn Gln Asn Asp Leu
1               5

<210> SEQ ID NO 48
<211> LENGTH: 9
<212> TYPE: PRT
<213> ORGANISM: Artificial
<220> FEATURE:
<223> OTHER INFORMATION: CLP-2456

<400> SEQUENCE: 48

Ser Val Ile Asn Gln Asn Asp Leu Ala
1               5

<210> SEQ ID NO 49
<211> LENGTH: 9
<212> TYPE: PRT
<213> ORGANISM: Artificial
<220> FEATURE:
<223> OTHER INFORMATION: CLP-2457
```

-continued

```
<400> SEQUENCE: 49

Phe Cys Asp Phe Arg Tyr Ser Lys Ser
1               5

<210> SEQ ID NO 50
<211> LENGTH: 9
<212> TYPE: PRT
<213> ORGANISM: Artificial
<220> FEATURE:
<223> OTHER INFORMATION: CLP-2458

<400> SEQUENCE: 50

Ser His Gly Pro Asp Val Ile Val Val
1               5

<210> SEQ ID NO 51
<211> LENGTH: 9
<212> TYPE: PRT
<213> ORGANISM: Artificial
<220> FEATURE:
<223> OTHER INFORMATION: CLP-2459

<400> SEQUENCE: 51

Pro Leu Leu Arg His Tyr Gln Gln Leu
1               5

<210> SEQ ID NO 52
<211> LENGTH: 9
<212> TYPE: PRT
<213> ORGANISM: Artificial
<220> FEATURE:
<223> OTHER INFORMATION: CLP-2460

<400> SEQUENCE: 52

Gly Leu Cys Ser Pro Glu Lys His Leu
1               5

<210> SEQ ID NO 53
<211> LENGTH: 9
<212> TYPE: PRT
<213> ORGANISM: Artificial
<220> FEATURE:
<223> OTHER INFORMATION: CLP-2461

<400> SEQUENCE: 53

His Leu Gly Glu Ile Thr Tyr Pro Phe
1               5

<210> SEQ ID NO 54
<211> LENGTH: 9
<212> TYPE: PRT
<213> ORGANISM: Artificial
<220> FEATURE:
<223> OTHER INFORMATION: CLP-2462

<400> SEQUENCE: 54

Leu Gly Glu Ile Thr Tyr Pro Phe Ala
1               5

<210> SEQ ID NO 55
<211> LENGTH: 9
<212> TYPE: PRT
<213> ORGANISM: Artificial
<220> FEATURE:
<223> OTHER INFORMATION: CLP-2463
```

```
<400> SEQUENCE: 55

His Cys Ala Leu Leu Leu His Leu
1               5

<210> SEQ ID NO 56
<211> LENGTH: 9
<212> TYPE: PRT
<213> ORGANISM: Artificial
<220> FEATURE:
<223> OTHER INFORMATION: CLP-2464

<400> SEQUENCE: 56

Ala Leu Leu Leu Leu His Leu Ser Pro
1               5

<210> SEQ ID NO 57
<211> LENGTH: 9
<212> TYPE: PRT
<213> ORGANISM: Artificial
<220> FEATURE:
<223> OTHER INFORMATION: CLP-2465

<400> SEQUENCE: 57

Leu Leu Leu Leu His Leu Ser Pro Gly
1               5

<210> SEQ ID NO 58
<211> LENGTH: 9
<212> TYPE: PRT
<213> ORGANISM: Artificial
<220> FEATURE:
<223> OTHER INFORMATION: CLP-2466

<400> SEQUENCE: 58

Leu Leu Leu His Leu Ser Pro Gly Ala
1               5

<210> SEQ ID NO 59
<211> LENGTH: 9
<212> TYPE: PRT
<213> ORGANISM: Artificial
<220> FEATURE:
<223> OTHER INFORMATION: CLP-2467

<400> SEQUENCE: 59

Leu Leu His Leu Ser Pro Gly Ala Ala
1               5

<210> SEQ ID NO 60
<211> LENGTH: 9
<212> TYPE: PRT
<213> ORGANISM: Artificial
<220> FEATURE:
<223> OTHER INFORMATION: CLP-2468

<400> SEQUENCE: 60

Phe Thr Thr Pro Asp Val Asp Val Leu
1               5

<210> SEQ ID NO 61
<211> LENGTH: 9
<212> TYPE: PRT
<213> ORGANISM: Artificial
<220> FEATURE:
<223> OTHER INFORMATION: CLP-2469

<400> SEQUENCE: 61
```

```
Thr Thr Pro Asp Val Asp Val Leu Leu
1               5

<210> SEQ ID NO 62
<211> LENGTH: 9
<212> TYPE: PRT
<213> ORGANISM: Artificial
<220> FEATURE:
<223> OTHER INFORMATION: CLP-2470

<400> SEQUENCE: 62

Val Leu Leu Phe His Tyr Glu Ser Val
1               5

<210> SEQ ID NO 63
<211> LENGTH: 9
<212> TYPE: PRT
<213> ORGANISM: Artificial
<220> FEATURE:
<223> OTHER INFORMATION: CLP-2471

<400> SEQUENCE: 63

Phe Ile Thr Gln Val Glu Glu Glu Ile
1               5

<210> SEQ ID NO 64
<211> LENGTH: 9
<212> TYPE: PRT
<213> ORGANISM: Artificial
<220> FEATURE:
<223> OTHER INFORMATION: CLP-2472

<400> SEQUENCE: 64

Phe Thr Ala Ala Asp Thr Gln Ser Leu
1               5

<210> SEQ ID NO 65
<211> LENGTH: 9
<212> TYPE: PRT
<213> ORGANISM: Artificial
<220> FEATURE:
<223> OTHER INFORMATION: CLP-2473

<400> SEQUENCE: 65

Ser Leu Leu Glu His Phe Asn Thr Val
1               5

<210> SEQ ID NO 66
<211> LENGTH: 9
<212> TYPE: PRT
<213> ORGANISM: Artificial
<220> FEATURE:
<223> OTHER INFORMATION: CLP-2474

<400> SEQUENCE: 66

Ser Thr Ile Lys Glu Glu Pro Lys Ile
1               5

<210> SEQ ID NO 67
<211> LENGTH: 9
<212> TYPE: PRT
<213> ORGANISM: Artificial
<220> FEATURE:
<223> OTHER INFORMATION: CLP-2475

<400> SEQUENCE: 67
```

```
Lys Ile Asp Phe Arg Val Tyr Asn Leu
1               5

<210> SEQ ID NO 68
<211> LENGTH: 9
<212> TYPE: PRT
<213> ORGANISM: Artificial
<220> FEATURE:
<223> OTHER INFORMATION: CLP-2476

<400> SEQUENCE: 68

Asn Leu Leu Thr Pro Asp Ser Lys Met
1               5

<210> SEQ ID NO 69
<211> LENGTH: 9
<212> TYPE: PRT
<213> ORGANISM: Artificial
<220> FEATURE:
<223> OTHER INFORMATION: CLP-2479

<400> SEQUENCE: 69

Val Thr Trp Arg Gly Ala Asp Ile Leu
1               5

<210> SEQ ID NO 70
<211> LENGTH: 9
<212> TYPE: PRT
<213> ORGANISM: Artificial
<220> FEATURE:
<223> OTHER INFORMATION: CLP-2480

<400> SEQUENCE: 70

Ile Leu Arg Gly Ser Pro Ser Tyr Thr
1               5

<210> SEQ ID NO 71
<211> LENGTH: 9
<212> TYPE: PRT
<213> ORGANISM: Artificial
<220> FEATURE:
<223> OTHER INFORMATION: CLP-2481

<400> SEQUENCE: 71

Tyr Thr Gln Ala Ser Leu Gly Leu Leu
1               5

<210> SEQ ID NO 72
<211> LENGTH: 9
<212> TYPE: PRT
<213> ORGANISM: Artificial
<220> FEATURE:
<223> OTHER INFORMATION: CLP-2482

<400> SEQUENCE: 72

Ala Ser Leu Gly Leu Leu Thr Pro Val
1               5

<210> SEQ ID NO 73
<211> LENGTH: 9
<212> TYPE: PRT
<213> ORGANISM: Artificial
<220> FEATURE:
<223> OTHER INFORMATION: CLP-2483

<400> SEQUENCE: 73

Gly Leu Leu Thr Pro Val Ser Gly Thr
```

-continued

```
1               5

<210> SEQ ID NO 74
<211> LENGTH: 9
<212> TYPE: PRT
<213> ORGANISM: Artificial
<220> FEATURE:
<223> OTHER INFORMATION: CLP-2484

<400> SEQUENCE: 74

Gly Thr Gln Glu Gln Thr Lys Thr Leu
1               5

<210> SEQ ID NO 75
<211> LENGTH: 9
<212> TYPE: PRT
<213> ORGANISM: Artificial
<220> FEATURE:
<223> OTHER INFORMATION: CLP-2485

<400> SEQUENCE: 75

Lys Thr Leu Arg Asp Ser Pro Asn Val
1               5

<210> SEQ ID NO 76
<211> LENGTH: 9
<212> TYPE: PRT
<213> ORGANISM: Artificial
<220> FEATURE:
<223> OTHER INFORMATION: CLP-2486

<400> SEQUENCE: 76

His Leu Ala Arg Pro Ile Tyr Gly Leu
1               5

<210> SEQ ID NO 77
<211> LENGTH: 9
<212> TYPE: PRT
<213> ORGANISM: Artificial
<220> FEATURE:
<223> OTHER INFORMATION: CLP-2487

<400> SEQUENCE: 77

Pro Ile Tyr Gly Leu Ala Val Glu Thr
1               5

<210> SEQ ID NO 78
<211> LENGTH: 9
<212> TYPE: PRT
<213> ORGANISM: Artificial
<220> FEATURE:
<223> OTHER INFORMATION: CLP-2488

<400> SEQUENCE: 78

Leu Ala Val Glu Thr Lys Gly Phe Leu
1               5

<210> SEQ ID NO 79
<211> LENGTH: 9
<212> TYPE: PRT
<213> ORGANISM: Artificial
<220> FEATURE:
<223> OTHER INFORMATION: CLP-2489

<400> SEQUENCE: 79

Phe Leu Gln Gly Ala Pro Ala Gly Gly
1               5
```

```
<210> SEQ ID NO 80
<211> LENGTH: 9
<212> TYPE: PRT
<213> ORGANISM: Artificial
<220> FEATURE:
<223> OTHER INFORMATION: CLP-2490

<400> SEQUENCE: 80

Ala Gly Gly Glu Lys Ser Gly Ala Leu
1               5

<210> SEQ ID NO 81
<211> LENGTH: 9
<212> TYPE: PRT
<213> ORGANISM: Artificial
<220> FEATURE:
<223> OTHER INFORMATION: CLP-2491

<400> SEQUENCE: 81

Gly Ala Leu Pro Gln Gln Tyr Pro Ala
1               5

<210> SEQ ID NO 82
<211> LENGTH: 9
<212> TYPE: PRT
<213> ORGANISM: Artificial
<220> FEATURE:
<223> OTHER INFORMATION: CLP-2492

<400> SEQUENCE: 82

Ala Leu Pro Gln Gln Tyr Pro Ala Ser
1               5

<210> SEQ ID NO 83
<211> LENGTH: 9
<212> TYPE: PRT
<213> ORGANISM: Artificial
<220> FEATURE:
<223> OTHER INFORMATION: CLP-2493

<400> SEQUENCE: 83

Phe Cys Ala Asn Cys Leu Thr Thr Lys
1               5

<210> SEQ ID NO 84
<211> LENGTH: 9
<212> TYPE: PRT
<213> ORGANISM: Artificial
<220> FEATURE:
<223> OTHER INFORMATION: CLP-2494

<400> SEQUENCE: 84

Ala Asn Gly Gly Tyr Val Cys Asn Ala
1               5

<210> SEQ ID NO 85
<211> LENGTH: 9
<212> TYPE: PRT
<213> ORGANISM: Artificial
<220> FEATURE:
<223> OTHER INFORMATION: CLP-2495

<400> SEQUENCE: 85

Asn Ala Cys Gly Leu Tyr Gln Lys Leu
1               5
```

```
<210> SEQ ID NO 86
<211> LENGTH: 9
<212> TYPE: PRT
<213> ORGANISM: Artificial
<220> FEATURE:
<223> OTHER INFORMATION: CLP-2496

<400> SEQUENCE: 86

Gly Leu Tyr Gln Lys Leu His Ser Thr
1               5

<210> SEQ ID NO 87
<211> LENGTH: 9
<212> TYPE: PRT
<213> ORGANISM: Artificial
<220> FEATURE:
<223> OTHER INFORMATION: CLP-2497

<400> SEQUENCE: 87

Lys Leu His Ser Thr Pro Arg Pro Leu
1               5

<210> SEQ ID NO 88
<211> LENGTH: 9
<212> TYPE: PRT
<213> ORGANISM: Artificial
<220> FEATURE:
<223> OTHER INFORMATION: CLP-2498

<400> SEQUENCE: 88

Ser Thr Pro Arg Pro Leu Asn Ile Ile
1               5

<210> SEQ ID NO 89
<211> LENGTH: 9
<212> TYPE: PRT
<213> ORGANISM: Artificial
<220> FEATURE:
<223> OTHER INFORMATION: CLP-2499

<400> SEQUENCE: 89

Arg Leu Asn Pro Glu Ala Leu Gln Ala
1               5

<210> SEQ ID NO 90
<211> LENGTH: 9
<212> TYPE: PRT
<213> ORGANISM: Artificial
<220> FEATURE:
<223> OTHER INFORMATION: CLP-2500

<400> SEQUENCE: 90

Val Leu Val Ser Gln Thr Leu Asp Ile
1               5

<210> SEQ ID NO 91
<211> LENGTH: 9
<212> TYPE: PRT
<213> ORGANISM: Artificial
<220> FEATURE:
<223> OTHER INFORMATION: CLP-2501

<400> SEQUENCE: 91

Asp Ile His Lys Arg Met Gln Pro Leu
1               5
```

```
<210> SEQ ID NO 92
<211> LENGTH: 9
<212> TYPE: PRT
<213> ORGANISM: Artificial
<220> FEATURE:
<223> OTHER INFORMATION: CLP-2502

<400> SEQUENCE: 92

Arg Met Gln Pro Leu His Ile Gln Ile
1               5

<210> SEQ ID NO 93
<211> LENGTH: 9
<212> TYPE: PRT
<213> ORGANISM: Artificial
<220> FEATURE:
<223> OTHER INFORMATION: CLP-2503

<400> SEQUENCE: 93

Tyr Pro Leu Phe Gly Leu Pro Phe Val
1               5

<210> SEQ ID NO 94
<211> LENGTH: 9
<212> TYPE: PRT
<213> ORGANISM: Artificial
<220> FEATURE:
<223> OTHER INFORMATION: CLP-2504

<400> SEQUENCE: 94

Gly Leu Pro Phe Val His Asn Asp Phe
1               5

<210> SEQ ID NO 95
<211> LENGTH: 9
<212> TYPE: PRT
<213> ORGANISM: Artificial
<220> FEATURE:
<223> OTHER INFORMATION: CLP-2505

<400> SEQUENCE: 95

Phe Val His Asn Asp Phe Gln Ser Glu
1               5

<210> SEQ ID NO 96
<211> LENGTH: 9
<212> TYPE: PRT
<213> ORGANISM: Artificial
<220> FEATURE:
<223> OTHER INFORMATION: CLP-2506

<400> SEQUENCE: 96

Ser Val Pro Gly Asn Pro His Tyr Leu
1               5

<210> SEQ ID NO 97
<211> LENGTH: 9
<212> TYPE: PRT
<213> ORGANISM: Artificial
<220> FEATURE:
<223> OTHER INFORMATION: CLP-2507

<400> SEQUENCE: 97

Gly Asn Pro His Tyr Leu Ser His Val
1               5

<210> SEQ ID NO 98
```

```
<211> LENGTH: 9
<212> TYPE: PRT
<213> ORGANISM: Artificial
<220> FEATURE:
<223> OTHER INFORMATION: CLP-2508

<400> SEQUENCE: 98

His Tyr Leu Ser His Val Pro Gly Leu
1               5

<210> SEQ ID NO 99
<211> LENGTH: 9
<212> TYPE: PRT
<213> ORGANISM: Artificial
<220> FEATURE:
<223> OTHER INFORMATION: CLP-2509

<400> SEQUENCE: 99

Tyr Val Pro Tyr Pro Thr Phe Asn Leu
1               5

<210> SEQ ID NO 100
<211> LENGTH: 9
<212> TYPE: PRT
<213> ORGANISM: Artificial
<220> FEATURE:
<223> OTHER INFORMATION: CLP-2510

<400> SEQUENCE: 100

Phe Asn Leu Pro Pro His Phe Ser Ala
1               5

<210> SEQ ID NO 101
<211> LENGTH: 9
<212> TYPE: PRT
<213> ORGANISM: Artificial
<220> FEATURE:
<223> OTHER INFORMATION: CLP-2511

<400> SEQUENCE: 101

Asn Leu Pro Pro His Phe Ser Ala Val
1               5

<210> SEQ ID NO 102
<211> LENGTH: 9
<212> TYPE: PRT
<213> ORGANISM: Artificial
<220> FEATURE:
<223> OTHER INFORMATION: CLP-2512

<400> SEQUENCE: 102

Ser Ala Val Gly Ser Asp Asn Asp Ile
1               5

<210> SEQ ID NO 103
<211> LENGTH: 9
<212> TYPE: PRT
<213> ORGANISM: Artificial
<220> FEATURE:
<223> OTHER INFORMATION: CLP-2513

<400> SEQUENCE: 103

Lys Asn Glu Gly Pro Leu Asn Val Val
1               5

<210> SEQ ID NO 104
<211> LENGTH: 9
```

```
<212> TYPE: PRT
<213> ORGANISM: Artificial
<220> FEATURE:
<223> OTHER INFORMATION: CLP-2514

<400> SEQUENCE: 104

Thr Lys Cys Val His Cys Gly Ile Val
1               5

<210> SEQ ID NO 105
<211> LENGTH: 9
<212> TYPE: PRT
<213> ORGANISM: Artificial
<220> FEATURE:
<223> OTHER INFORMATION: CLP-2515

<400> SEQUENCE: 105

Cys Val His Cys Gly Ile Val Phe Leu
1               5

<210> SEQ ID NO 106
<211> LENGTH: 9
<212> TYPE: PRT
<213> ORGANISM: Artificial
<220> FEATURE:
<223> OTHER INFORMATION: CLP-2516

<400> SEQUENCE: 106

Cys Gly Ile Val Phe Leu Asp Glu Val
1               5

<210> SEQ ID NO 107
<211> LENGTH: 9
<212> TYPE: PRT
<213> ORGANISM: Artificial
<220> FEATURE:
<223> OTHER INFORMATION: CLP-2517

<400> SEQUENCE: 107

Phe Leu Asp Glu Val Met Tyr Ala Leu
1               5

<210> SEQ ID NO 108
<211> LENGTH: 9
<212> TYPE: PRT
<213> ORGANISM: Artificial
<220> FEATURE:
<223> OTHER INFORMATION: CLP-2518

<400> SEQUENCE: 108

Val Met Tyr Ala Leu His Met Ser Cys
1               5

<210> SEQ ID NO 109
<211> LENGTH: 9
<212> TYPE: PRT
<213> ORGANISM: Artificial
<220> FEATURE:
<223> OTHER INFORMATION: CLP-2519

<400> SEQUENCE: 109

Phe Gln Cys Ser Ile Cys Gln His Leu
1               5

<210> SEQ ID NO 110
<211> LENGTH: 9
<212> TYPE: PRT
```

```
<213> ORGANISM: Artificial
<220> FEATURE:
<223> OTHER INFORMATION: CLP-2520

<400> SEQUENCE: 110

Gly Leu His Arg Asn Asn Ala Gln Val
1               5

<210> SEQ ID NO 111
<211> LENGTH: 9
<212> TYPE: PRT
<213> ORGANISM: Artificial
<220> FEATURE:
<223> OTHER INFORMATION: CLP-2477

<400> SEQUENCE: 111

Lys Met Gly Glu Pro Val Ser Glu Ser
1               5

<210> SEQ ID NO 112
<211> LENGTH: 9
<212> TYPE: PRT
<213> ORGANISM: Artificial
<220> FEATURE:
<223> OTHER INFORMATION: CLP-2478

<400> SEQUENCE: 112

Gly Leu Lys Glu Lys Val Trp Thr Glu
1               5

<210> SEQ ID NO 113
<211> LENGTH: 39
<212> TYPE: DNA
<213> ORGANISM: Artificial
<220> FEATURE:
<223> OTHER INFORMATION: Primer, 9616SXC

<400> SEQUENCE: 113
cagtacggat ccaccatggc cgagctgcgc ctgaagggc                        39

<210> SEQ ID NO 114
<211> LENGTH: 38
<212> TYPE: DNA
<213> ORGANISM: Artificial
<220> FEATURE:
<223> OTHER INFORMATION: Primer, 9617SXC

<400> SEQUENCE: 114
ccacgaggat ccttaggaga atattcggat ggcttgcg                         38

<210> SEQ ID NO 115
<211> LENGTH: 20
<212> TYPE: DNA
<213> ORGANISM: Artificial
<220> FEATURE:
<223> OTHER INFORMATION: Primer, 9620MC

<400> SEQUENCE: 115
taatacgact cactataggg                                             20

<210> SEQ ID NO 116
<211> LENGTH: 18
<212> TYPE: DNA
<213> ORGANISM: Artificial
<220> FEATURE:
<223> OTHER INFORMATION: Primer, 9621MC
```

<400> SEQUENCE: 116
tagaaggcac agtcgagg                                                18

<210> SEQ ID NO 117
<211> LENGTH: 23
<212> TYPE: DNA
<213> ORGANISM: Artificial
<220> FEATURE:
<223> OTHER INFORMATION: Primer, 9618MC

<400> SEQUENCE: 117
gaaaacgact tcctggcggg gag                                          23

<210> SEQ ID NO 118
<211> LENGTH: 22
<212> TYPE: DNA
<213> ORGANISM: Artificial
<220> FEATURE:
<223> OTHER INFORMATION: Primer, 9619MC

<400> SEQUENCE: 118
gctcacccag gcgtggggcc tc                                           22

<210> SEQ ID NO 119
<211> LENGTH: 9
<212> TYPE: PRT
<213> ORGANISM: Artificial
<220> FEATURE:
<223> OTHER INFORMATION: CLP-2599

<400> SEQUENCE: 119

Val Pro Val Pro Thr Ser Glu His Val
1               5

<210> SEQ ID NO 120
<211> LENGTH: 9
<212> TYPE: PRT
<213> ORGANISM: Artificial
<220> FEATURE:
<223> OTHER INFORMATION: CLP-2602

<400> SEQUENCE: 120

Pro Thr Ser Glu His Val Ala Glu Ile
1               5

<210> SEQ ID NO 121
<211> LENGTH: 9
<212> TYPE: PRT
<213> ORGANISM: Artificial
<220> FEATURE:
<223> OTHER INFORMATION: CLP-2609

<400> SEQUENCE: 121

Glu Ile Val Gly Arg Gln Cys Lys Ile
1               5

<210> SEQ ID NO 122
<211> LENGTH: 9
<212> TYPE: PRT
<213> ORGANISM: Artificial
<220> FEATURE:
<223> OTHER INFORMATION: CLP-2616

<400> SEQUENCE: 122

Lys Ile Lys Ala Leu Arg Ala Lys Thr
1               5

<210> SEQ ID NO 123
<211> LENGTH: 9
<212> TYPE: PRT
<213> ORGANISM: Artificial
<220> FEATURE:
<223> OTHER INFORMATION: CLP-2618

<400> SEQUENCE: 123

Lys Ala Leu Arg Ala Lys Thr Asn Thr
1               5

<210> SEQ ID NO 124
<211> LENGTH: 9
<212> TYPE: PRT
<213> ORGANISM: Artificial
<220> FEATURE:
<223> OTHER INFORMATION: CLP-2619

<400> SEQUENCE: 124

Ala Leu Arg Ala Lys Thr Asn Thr Tyr
1               5

<210> SEQ ID NO 125
<211> LENGTH: 9
<212> TYPE: PRT
<213> ORGANISM: Artificial
<220> FEATURE:
<223> OTHER INFORMATION: CLP-2620

<400> SEQUENCE: 125

Leu Arg Ala Lys Thr Asn Thr Tyr Ile
1               5

<210> SEQ ID NO 126
<211> LENGTH: 9
<212> TYPE: PRT
<213> ORGANISM: Artificial
<220> FEATURE:
<223> OTHER INFORMATION: CLP-2624

<400> SEQUENCE: 126

Thr Asn Thr Tyr Ile Lys Thr Pro Val
1               5

<210> SEQ ID NO 127
<211> LENGTH: 9
<212> TYPE: PRT
<213> ORGANISM: Artificial
<220> FEATURE:
<223> OTHER INFORMATION: CLP-2627

<400> SEQUENCE: 127

Tyr Ile Lys Thr Pro Val Arg Gly Glu
1               5

<210> SEQ ID NO 128
<211> LENGTH: 9
<212> TYPE: PRT
<213> ORGANISM: Artificial
<220> FEATURE:
<223> OTHER INFORMATION: CLP-2630

<400> SEQUENCE: 128

Thr Pro Val Arg Gly Glu Glu Pro Val
1               5

-continued

```
<210> SEQ ID NO 129
<211> LENGTH: 9
<212> TYPE: PRT
<213> ORGANISM: Artificial
<220> FEATURE:
<223> OTHER INFORMATION: CLP-2633

<400> SEQUENCE: 129

Arg Gly Glu Glu Pro Val Phe Met Val
1               5

<210> SEQ ID NO 130
<211> LENGTH: 9
<212> TYPE: PRT
<213> ORGANISM: Artificial
<220> FEATURE:
<223> OTHER INFORMATION: CLP-2640

<400> SEQUENCE: 130

Met Val Thr Gly Arg Arg Glu Asp Val
1               5

<210> SEQ ID NO 131
<211> LENGTH: 9
<212> TYPE: PRT
<213> ORGANISM: Artificial
<220> FEATURE:
<223> OTHER INFORMATION: CLP-2641

<400> SEQUENCE: 131

Val Thr Gly Arg Arg Glu Asp Val Ala
1               5

<210> SEQ ID NO 132
<211> LENGTH: 9
<212> TYPE: PRT
<213> ORGANISM: Artificial
<220> FEATURE:
<223> OTHER INFORMATION: CLP-2643

<400> SEQUENCE: 132

Gly Arg Arg Glu Asp Val Ala Thr Ala
1               5

<210> SEQ ID NO 133
<211> LENGTH: 9
<212> TYPE: PRT
<213> ORGANISM: Artificial
<220> FEATURE:
<223> OTHER INFORMATION: CLP-2647

<400> SEQUENCE: 133

Asp Val Ala Thr Ala Arg Arg Glu Ile
1               5

<210> SEQ ID NO 134
<211> LENGTH: 9
<212> TYPE: PRT
<213> ORGANISM: Artificial
<220> FEATURE:
<223> OTHER INFORMATION: CLP-2648

<400> SEQUENCE: 134

Val Ala Thr Ala Arg Arg Glu Ile Ile
1               5
```

```
<210> SEQ ID NO 135
<211> LENGTH: 9
<212> TYPE: PRT
<213> ORGANISM: Artificial
<220> FEATURE:
<223> OTHER INFORMATION: CLP-2650

<400> SEQUENCE: 135

Thr Ala Arg Arg Glu Ile Ile Ser Ala
1               5

<210> SEQ ID NO 136
<211> LENGTH: 9
<212> TYPE: PRT
<213> ORGANISM: Artificial
<220> FEATURE:
<223> OTHER INFORMATION: CLP-2651

<400> SEQUENCE: 136

Ala Arg Arg Glu Ile Ile Ser Ala Ala
1               5

<210> SEQ ID NO 137
<211> LENGTH: 9
<212> TYPE: PRT
<213> ORGANISM: Artificial
<220> FEATURE:
<223> OTHER INFORMATION: CLP-2655

<400> SEQUENCE: 137

Ile Ile Ser Ala Ala Glu His Phe Ser
1               5

<210> SEQ ID NO 138
<211> LENGTH: 9
<212> TYPE: PRT
<213> ORGANISM: Artificial
<220> FEATURE:
<223> OTHER INFORMATION: CLP-2656

<400> SEQUENCE: 138

Ile Ser Ala Ala Glu His Phe Ser Met
1               5

<210> SEQ ID NO 139
<211> LENGTH: 9
<212> TYPE: PRT
<213> ORGANISM: Artificial
<220> FEATURE:
<223> OTHER INFORMATION: CLP-2657

<400> SEQUENCE: 139

Ser Ala Ala Glu His Phe Ser Met Ile
1               5

<210> SEQ ID NO 140
<211> LENGTH: 9
<212> TYPE: PRT
<213> ORGANISM: Artificial
<220> FEATURE:
<223> OTHER INFORMATION: CLP-2659

<400> SEQUENCE: 140

Ala Glu His Phe Ser Met Ile Arg Ala
1               5

<210> SEQ ID NO 141
```

```
<211> LENGTH: 9
<212> TYPE: PRT
<213> ORGANISM: Artificial
<220> FEATURE:
<223> OTHER INFORMATION: CLP-2663

<400> SEQUENCE: 141

Ser Met Ile Arg Ala Ser Arg Asn Lys
1               5

<210> SEQ ID NO 142
<211> LENGTH: 9
<212> TYPE: PRT
<213> ORGANISM: Artificial
<220> FEATURE:
<223> OTHER INFORMATION: CLP-2666

<400> SEQUENCE: 142

Arg Ala Ser Arg Asn Lys Ser Gly Ala
1               5

<210> SEQ ID NO 143
<211> LENGTH: 9
<212> TYPE: PRT
<213> ORGANISM: Artificial
<220> FEATURE:
<223> OTHER INFORMATION: CLP-2670

<400> SEQUENCE: 143

Asn Lys Ser Gly Ala Ala Phe Gly Val
1               5

<210> SEQ ID NO 144
<211> LENGTH: 9
<212> TYPE: PRT
<213> ORGANISM: Artificial
<220> FEATURE:
<223> OTHER INFORMATION: CLP-2673

<400> SEQUENCE: 144

Gly Ala Ala Phe Gly Val Ala Pro Ala
1               5

<210> SEQ ID NO 145
<211> LENGTH: 9
<212> TYPE: PRT
<213> ORGANISM: Artificial
<220> FEATURE:
<223> OTHER INFORMATION: CLP-2674

<400> SEQUENCE: 145

Ala Ala Phe Gly Val Ala Pro Ala Leu
1               5

<210> SEQ ID NO 146
<211> LENGTH: 9
<212> TYPE: PRT
<213> ORGANISM: Artificial
<220> FEATURE:
<223> OTHER INFORMATION: CLP-2677

<400> SEQUENCE: 146

Gly Val Ala Pro Ala Leu Pro Gly Gln
1               5

<210> SEQ ID NO 147
<211> LENGTH: 9
```

```
<212> TYPE: PRT
<213> ORGANISM: Artificial
<220> FEATURE:
<223> OTHER INFORMATION: CLP-2678

<400> SEQUENCE: 147

Val Ala Pro Ala Leu Pro Gly Gln Val
1               5

<210> SEQ ID NO 148
<211> LENGTH: 9
<212> TYPE: PRT
<213> ORGANISM: Artificial
<220> FEATURE:
<223> OTHER INFORMATION: CLP-2680

<400> SEQUENCE: 148

Pro Ala Leu Pro Gly Gln Val Thr Ile
1               5

<210> SEQ ID NO 149
<211> LENGTH: 9
<212> TYPE: PRT
<213> ORGANISM: Artificial
<220> FEATURE:
<223> OTHER INFORMATION: CLP-2681

<400> SEQUENCE: 149

Ala Leu Pro Gly Gln Val Thr Ile Arg
1               5

<210> SEQ ID NO 150
<211> LENGTH: 9
<212> TYPE: PRT
<213> ORGANISM: Artificial
<220> FEATURE:
<223> OTHER INFORMATION: CLP-2682

<400> SEQUENCE: 150

Leu Pro Gly Gln Val Thr Ile Arg Val
1               5

<210> SEQ ID NO 151
<211> LENGTH: 9
<212> TYPE: PRT
<213> ORGANISM: Artificial
<220> FEATURE:
<223> OTHER INFORMATION: CLP-2684

<400> SEQUENCE: 151

Gly Gln Val Thr Ile Arg Val Arg Val
1               5

<210> SEQ ID NO 152
<211> LENGTH: 9
<212> TYPE: PRT
<213> ORGANISM: Artificial
<220> FEATURE:
<223> OTHER INFORMATION: CLP-2689

<400> SEQUENCE: 152

Arg Val Arg Val Pro Tyr Arg Val Val
1               5

<210> SEQ ID NO 153
<211> LENGTH: 9
<212> TYPE: PRT
```

```
<213> ORGANISM: Artificial
<220> FEATURE:
<223> OTHER INFORMATION: CLP-2691

<400> SEQUENCE: 153

Arg Val Pro Tyr Arg Val Val Gly Leu
1               5

<210> SEQ ID NO 154
<211> LENGTH: 9
<212> TYPE: PRT
<213> ORGANISM: Artificial
<220> FEATURE:
<223> OTHER INFORMATION: CLP-2692

<400> SEQUENCE: 154

Val Pro Tyr Arg Val Val Gly Leu Val
1               5

<210> SEQ ID NO 155
<211> LENGTH: 9
<212> TYPE: PRT
<213> ORGANISM: Artificial
<220> FEATURE:
<223> OTHER INFORMATION: CLP-2695

<400> SEQUENCE: 155

Arg Val Val Gly Leu Val Val Gly Pro
1               5

<210> SEQ ID NO 156
<211> LENGTH: 9
<212> TYPE: PRT
<213> ORGANISM: Artificial
<220> FEATURE:
<223> OTHER INFORMATION: CLP-2698

<400> SEQUENCE: 156

Gly Leu Val Val Gly Pro Lys Gly Ala
1               5

<210> SEQ ID NO 157
<211> LENGTH: 9
<212> TYPE: PRT
<213> ORGANISM: Artificial
<220> FEATURE:
<223> OTHER INFORMATION: CLP-2699

<400> SEQUENCE: 157

Leu Val Val Gly Pro Lys Gly Ala Thr
1               5

<210> SEQ ID NO 158
<211> LENGTH: 9
<212> TYPE: PRT
<213> ORGANISM: Artificial
<220> FEATURE:
<223> OTHER INFORMATION: CLP-2700

<400> SEQUENCE: 158

Val Val Gly Pro Lys Gly Ala Thr Ile
1               5

<210> SEQ ID NO 159
<211> LENGTH: 9
<212> TYPE: PRT
<213> ORGANISM: Artificial
```

```
<220> FEATURE:
<223> OTHER INFORMATION: CLP-2710

<400> SEQUENCE: 159

Arg Ile Gln Gln Gln Thr Asn Thr Tyr
1               5

<210> SEQ ID NO 160
<211> LENGTH: 9
<212> TYPE: PRT
<213> ORGANISM: Artificial
<220> FEATURE:
<223> OTHER INFORMATION: CLP-2711

<400> SEQUENCE: 160

Ile Gln Gln Gln Thr Asn Thr Tyr Ile
1               5

<210> SEQ ID NO 161
<211> LENGTH: 9
<212> TYPE: PRT
<213> ORGANISM: Artificial
<220> FEATURE:
<223> OTHER INFORMATION: CLP-2712

<400> SEQUENCE: 161

Gln Gln Gln Thr Asn Thr Tyr Ile Ile
1               5

<210> SEQ ID NO 162
<211> LENGTH: 9
<212> TYPE: PRT
<213> ORGANISM: Artificial
<220> FEATURE:
<223> OTHER INFORMATION: CLP-2713

<400> SEQUENCE: 162

Gln Gln Thr Asn Thr Tyr Ile Ile Thr
1               5

<210> SEQ ID NO 163
<211> LENGTH: 9
<212> TYPE: PRT
<213> ORGANISM: Artificial
<220> FEATURE:
<223> OTHER INFORMATION: CLP-2718

<400> SEQUENCE: 163

Tyr Ile Ile Thr Pro Ser Arg Asp Arg
1               5

<210> SEQ ID NO 164
<211> LENGTH: 9
<212> TYPE: PRT
<213> ORGANISM: Artificial
<220> FEATURE:
<223> OTHER INFORMATION: CLP-2721

<400> SEQUENCE: 164

Thr Pro Ser Arg Asp Arg Asp Pro Val
1               5

<210> SEQ ID NO 165
<211> LENGTH: 9
<212> TYPE: PRT
<213> ORGANISM: Artificial
<220> FEATURE:
```

-continued

<223> OTHER INFORMATION: CLP-2724

<400> SEQUENCE: 165

Arg Asp Arg Asp Pro Val Phe Glu Ile
1               5

<210> SEQ ID NO 166
<211> LENGTH: 9
<212> TYPE: PRT
<213> ORGANISM: Artificial
<220> FEATURE:
<223> OTHER INFORMATION: CLP-2731

<400> SEQUENCE: 166

Glu Ile Thr Gly Ala Pro Gly Asn Val
1               5

<210> SEQ ID NO 167
<211> LENGTH: 9
<212> TYPE: PRT
<213> ORGANISM: Artificial
<220> FEATURE:
<223> OTHER INFORMATION: CLP-2734

<400> SEQUENCE: 167

Gly Ala Pro Gly Asn Val Glu Arg Ala
1               5

<210> SEQ ID NO 168
<211> LENGTH: 9
<212> TYPE: PRT
<213> ORGANISM: Artificial
<220> FEATURE:
<223> OTHER INFORMATION: CLP-2738

<400> SEQUENCE: 168

Asn Val Glu Arg Ala Arg Glu Glu Ile
1               5

<210> SEQ ID NO 169
<211> LENGTH: 9
<212> TYPE: PRT
<213> ORGANISM: Artificial
<220> FEATURE:
<223> OTHER INFORMATION: CLP-2744

<400> SEQUENCE: 169

Glu Glu Ile Glu Thr His Ile Ala Val
1               5

<210> SEQ ID NO 170
<211> LENGTH: 9
<212> TYPE: PRT
<213> ORGANISM: Artificial
<220> FEATURE:
<223> OTHER INFORMATION: CLP-2746

<400> SEQUENCE: 170

Ile Glu Thr His Ile Ala Val Arg Thr
1               5

<210> SEQ ID NO 171
<211> LENGTH: 9
<212> TYPE: PRT
<213> ORGANISM: Artificial
<220> FEATURE:
<223> OTHER INFORMATION: CLP-2749

```
<400> SEQUENCE: 171

His Ile Ala Val Arg Thr Gly Lys Ile
1               5

<210> SEQ ID NO 172
<211> LENGTH: 9
<212> TYPE: PRT
<213> ORGANISM: Artificial
<220> FEATURE:
<223> OTHER INFORMATION: CLP-2750

<400> SEQUENCE: 172

Ile Ala Val Arg Thr Gly Lys Ile Leu
1               5

<210> SEQ ID NO 173
<211> LENGTH: 9
<212> TYPE: PRT
<213> ORGANISM: Artificial
<220> FEATURE:
<223> OTHER INFORMATION: CLP-2756

<400> SEQUENCE: 173

Lys Ile Leu Glu Tyr Asn Asn Glu Asn
1               5

<210> SEQ ID NO 174
<211> LENGTH: 9
<212> TYPE: PRT
<213> ORGANISM: Artificial
<220> FEATURE:
<223> OTHER INFORMATION: CLP-2760

<400> SEQUENCE: 174

Tyr Asn Asn Glu Asn Asp Phe Leu Ala
1               5

<210> SEQ ID NO 175
<211> LENGTH: 9
<212> TYPE: PRT
<213> ORGANISM: Artificial
<220> FEATURE:
<223> OTHER INFORMATION: CLP-2762

<400> SEQUENCE: 175

Asn Glu Asn Asp Phe Leu Ala Gly Ser
1               5

<210> SEQ ID NO 176
<211> LENGTH: 9
<212> TYPE: PRT
<213> ORGANISM: Artificial
<220> FEATURE:
<223> OTHER INFORMATION: CLP-2766

<400> SEQUENCE: 176

Phe Leu Ala Gly Ser Pro Asp Ala Ala
1               5

<210> SEQ ID NO 177
<211> LENGTH: 9
<212> TYPE: PRT
<213> ORGANISM: Artificial
<220> FEATURE:
<223> OTHER INFORMATION: CLP-2767
```

```
<400> SEQUENCE: 177

Leu Ala Gly Ser Pro Asp Ala Ala Ile
1               5

<210> SEQ ID NO 178
<211> LENGTH: 9
<212> TYPE: PRT
<213> ORGANISM: Artificial
<220> FEATURE:
<223> OTHER INFORMATION: CLP-2774

<400> SEQUENCE: 178

Ala Ile Asp Ser Arg Tyr Ser Asp Ala
1               5

<210> SEQ ID NO 179
<211> LENGTH: 9
<212> TYPE: PRT
<213> ORGANISM: Artificial
<220> FEATURE:
<223> OTHER INFORMATION: CLP-2777

<400> SEQUENCE: 179

Ser Arg Tyr Ser Asp Ala Trp Arg Val
1               5

<210> SEQ ID NO 180
<211> LENGTH: 9
<212> TYPE: PRT
<213> ORGANISM: Artificial
<220> FEATURE:
<223> OTHER INFORMATION: CLP-2785

<400> SEQUENCE: 180

Val His Gln Pro Gly Cys Lys Pro Leu
1               5

<210> SEQ ID NO 181
<211> LENGTH: 9
<212> TYPE: PRT
<213> ORGANISM: Artificial
<220> FEATURE:
<223> OTHER INFORMATION: CLP-2793

<400> SEQUENCE: 181

Leu Ser Thr Phe Arg Gln Asn Ser Leu
1               5

<210> SEQ ID NO 182
<211> LENGTH: 9
<212> TYPE: PRT
<213> ORGANISM: Artificial
<220> FEATURE:
<223> OTHER INFORMATION: CLP-2801

<400> SEQUENCE: 182

Leu Gly Cys Ile Gly Glu Cys Gly Val
1               5

<210> SEQ ID NO 183
<211> LENGTH: 9
<212> TYPE: PRT
<213> ORGANISM: Artificial
<220> FEATURE:
<223> OTHER INFORMATION: CLP-2807

<400> SEQUENCE: 183
```

Cys Gly Val Asp Ser Gly Phe Glu Ala
1               5

<210> SEQ ID NO 184
<211> LENGTH: 9
<212> TYPE: PRT
<213> ORGANISM: Artificial
<220> FEATURE:
<223> OTHER INFORMATION: CLP-2812

<400> SEQUENCE: 184

Gly Phe Glu Ala Pro Arg Leu Asp Val
1               5

<210> SEQ ID NO 185
<211> LENGTH: 9
<212> TYPE: PRT
<213> ORGANISM: Artificial
<220> FEATURE:
<223> OTHER INFORMATION: CLP-2817

<400> SEQUENCE: 185

Arg Leu Asp Val Tyr Tyr Gly Val Ala
1               5

<210> SEQ ID NO 186
<211> LENGTH: 9
<212> TYPE: PRT
<213> ORGANISM: Artificial
<220> FEATURE:
<223> OTHER INFORMATION: CLP-2819

<400> SEQUENCE: 186

Asp Val Tyr Tyr Gly Val Ala Glu Thr
1               5

<210> SEQ ID NO 187
<211> LENGTH: 9
<212> TYPE: PRT
<213> ORGANISM: Artificial
<220> FEATURE:
<223> OTHER INFORMATION: CLP-2823

<400> SEQUENCE: 187

Gly Val Ala Glu Thr Ser Pro Pro Leu
1               5

<210> SEQ ID NO 188
<211> LENGTH: 9
<212> TYPE: PRT
<213> ORGANISM: Artificial
<220> FEATURE:
<223> OTHER INFORMATION: CLP-2825

<400> SEQUENCE: 188

Ala Glu Thr Ser Pro Pro Leu Trp Ala
1               5

<210> SEQ ID NO 189
<211> LENGTH: 9
<212> TYPE: PRT
<213> ORGANISM: Artificial
<220> FEATURE:
<223> OTHER INFORMATION: CLP-2830

<400> SEQUENCE: 189

```
Pro Leu Trp Ala Gly Gln Glu Asn Ala
1               5
```

<210> SEQ ID NO 190
<211> LENGTH: 9
<212> TYPE: PRT
<213> ORGANISM: Artificial
<220> FEATURE:
<223> OTHER INFORMATION: CLP-2833

<400> SEQUENCE: 190

```
Ala Gly Gln Glu Asn Ala Thr Pro Thr
1               5
```

<210> SEQ ID NO 191
<211> LENGTH: 9
<212> TYPE: PRT
<213> ORGANISM: Artificial
<220> FEATURE:
<223> OTHER INFORMATION: CLP-2835

<400> SEQUENCE: 191

```
Gln Glu Asn Ala Thr Pro Thr Ser Val
1               5
```

<210> SEQ ID NO 192
<211> LENGTH: 9
<212> TYPE: PRT
<213> ORGANISM: Artificial
<220> FEATURE:
<223> OTHER INFORMATION: CLP-2843

<400> SEQUENCE: 192

```
Val Leu Phe Ser Ser Ala Ser Ser Ser
1               5
```

<210> SEQ ID NO 193
<211> LENGTH: 9
<212> TYPE: PRT
<213> ORGANISM: Artificial
<220> FEATURE:
<223> OTHER INFORMATION: CLP-2857

<400> SEQUENCE: 193

```
Lys Ala Arg Ala Gly Pro Pro Gly Ala
1               5
```

<210> SEQ ID NO 194
<211> LENGTH: 9
<212> TYPE: PRT
<213> ORGANISM: Artificial
<220> FEATURE:
<223> OTHER INFORMATION: CLP-2869

<400> SEQUENCE: 194

```
Pro Ala Thr Ser Ala Gly Pro Glu Leu
1               5
```

<210> SEQ ID NO 195
<211> LENGTH: 9
<212> TYPE: PRT
<213> ORGANISM: Artificial
<220> FEATURE:
<223> OTHER INFORMATION: CLP-2870

<400> SEQUENCE: 195

```
Ala Thr Ser Ala Gly Pro Glu Leu Ala
```

-continued

```
1               5

<210> SEQ ID NO 196
<211> LENGTH: 9
<212> TYPE: PRT
<213> ORGANISM: Artificial
<220> FEATURE:
<223> OTHER INFORMATION: CLP-2872

<400> SEQUENCE: 196

Ser Ala Gly Pro Glu Leu Ala Gly Leu
1               5

<210> SEQ ID NO 197
<211> LENGTH: 9
<212> TYPE: PRT
<213> ORGANISM: Artificial
<220> FEATURE:
<223> OTHER INFORMATION: CLP-2879

<400> SEQUENCE: 197

Gly Leu Pro Arg Arg Pro Pro Gly Glu
1               5

<210> SEQ ID NO 198
<211> LENGTH: 9
<212> TYPE: PRT
<213> ORGANISM: Artificial
<220> FEATURE:
<223> OTHER INFORMATION: CLP-2887

<400> SEQUENCE: 198

Glu Pro Leu Gln Gly Phe Ser Lys Leu
1               5

<210> SEQ ID NO 199
<211> LENGTH: 9
<212> TYPE: PRT
<213> ORGANISM: Artificial
<220> FEATURE:
<223> OTHER INFORMATION: CLP-2892

<400> SEQUENCE: 199

Phe Ser Lys Leu Gly Gly Gly Gly Leu
1               5

<210> SEQ ID NO 200
<211> LENGTH: 9
<212> TYPE: PRT
<213> ORGANISM: Artificial
<220> FEATURE:
<223> OTHER INFORMATION: CLP-2894

<400> SEQUENCE: 200

Lys Leu Gly Gly Gly Gly Leu Arg Ser
1               5

<210> SEQ ID NO 201
<211> LENGTH: 9
<212> TYPE: PRT
<213> ORGANISM: Artificial
<220> FEATURE:
<223> OTHER INFORMATION: CLP-2899

<400> SEQUENCE: 201

Gly Leu Arg Ser Pro Gly Gly Gly Arg
1               5
```

<210> SEQ ID NO 202
<211> LENGTH: 9
<212> TYPE: PRT
<213> ORGANISM: Artificial
<220> FEATURE:
<223> OTHER INFORMATION: CLP-2909

<400> SEQUENCE: 202

Cys Met Val Cys Phe Glu Ser Glu Val
1               5

<210> SEQ ID NO 203
<211> LENGTH: 9
<212> TYPE: PRT
<213> ORGANISM: Artificial
<220> FEATURE:
<223> OTHER INFORMATION: CLP-2910

<400> SEQUENCE: 203

Met Val Cys Phe Glu Ser Glu Val Thr
1               5

<210> SEQ ID NO 204
<211> LENGTH: 9
<212> TYPE: PRT
<213> ORGANISM: Artificial
<220> FEATURE:
<223> OTHER INFORMATION: CLP-2911

<400> SEQUENCE: 204

Val Cys Phe Glu Ser Glu Val Thr Ala
1               5

<210> SEQ ID NO 205
<211> LENGTH: 9
<212> TYPE: PRT
<213> ORGANISM: Artificial
<220> FEATURE:
<223> OTHER INFORMATION: CLP-2913

<400> SEQUENCE: 205

Phe Glu Ser Glu Val Thr Ala Ala Leu
1               5

<210> SEQ ID NO 206
<211> LENGTH: 9
<212> TYPE: PRT
<213> ORGANISM: Artificial
<220> FEATURE:
<223> OTHER INFORMATION: CLP-2916

<400> SEQUENCE: 206

Glu Val Thr Ala Ala Leu Val Pro Cys
1               5

<210> SEQ ID NO 207
<211> LENGTH: 9
<212> TYPE: PRT
<213> ORGANISM: Artificial
<220> FEATURE:
<223> OTHER INFORMATION: CLP-2917

<400> SEQUENCE: 207

Val Thr Ala Ala Leu Val Pro Cys Gly
1               5

```
<210> SEQ ID NO 208
<211> LENGTH: 9
<212> TYPE: PRT
<213> ORGANISM: Artificial
<220> FEATURE:
<223> OTHER INFORMATION: CLP-2920

<400> SEQUENCE: 208

Ala Leu Val Pro Cys Gly His Asn Leu
1               5

<210> SEQ ID NO 209
<211> LENGTH: 9
<212> TYPE: PRT
<213> ORGANISM: Artificial
<220> FEATURE:
<223> OTHER INFORMATION: CLP-2921

<400> SEQUENCE: 209

Leu Val Pro Cys Gly His Asn Leu Phe
1               5

<210> SEQ ID NO 210
<211> LENGTH: 9
<212> TYPE: PRT
<213> ORGANISM: Artificial
<220> FEATURE:
<223> OTHER INFORMATION: CLP-2922

<400> SEQUENCE: 210

Val Pro Cys Gly His Asn Leu Phe Cys
1               5

<210> SEQ ID NO 211
<211> LENGTH: 9
<212> TYPE: PRT
<213> ORGANISM: Artificial
<220> FEATURE:
<223> OTHER INFORMATION: CLP-2927

<400> SEQUENCE: 211

Asn Leu Phe Cys Met Glu Cys Ala Val
1               5

<210> SEQ ID NO 212
<211> LENGTH: 9
<212> TYPE: PRT
<213> ORGANISM: Artificial
<220> FEATURE:
<223> OTHER INFORMATION: CLP-2929

<400> SEQUENCE: 212

Phe Cys Met Glu Cys Ala Val Arg Ile
1               5

<210> SEQ ID NO 213
<211> LENGTH: 9
<212> TYPE: PRT
<213> ORGANISM: Artificial
<220> FEATURE:
<223> OTHER INFORMATION: CLP-2933

<400> SEQUENCE: 213
```

```
Cys Ala Val Arg Ile Cys Glu Arg Thr
1               5

<210> SEQ ID NO 214
<211> LENGTH: 9
<212> TYPE: PRT
<213> ORGANISM: Artificial
<220> FEATURE:
<223> OTHER INFORMATION: CLP-2936

<400> SEQUENCE: 214

Arg Ile Cys Glu Arg Thr Asp Pro Glu
1               5

<210> SEQ ID NO 215
<211> LENGTH: 9
<212> TYPE: PRT
<213> ORGANISM: Artificial
<220> FEATURE:
<223> OTHER INFORMATION: CLP-2940

<400> SEQUENCE: 215

Arg Thr Asp Pro Glu Cys Pro Val Cys
1               5

<210> SEQ ID NO 216
<211> LENGTH: 9
<212> TYPE: PRT
<213> ORGANISM: Artificial
<220> FEATURE:
<223> OTHER INFORMATION: CLP-2945

<400> SEQUENCE: 216

Cys Pro Val Cys His Ile Thr Ala Thr
1               5

<210> SEQ ID NO 217
<211> LENGTH: 9
<212> TYPE: PRT
<213> ORGANISM: Artificial
<220> FEATURE:
<223> OTHER INFORMATION: CLP-2947

<400> SEQUENCE: 217

Val Cys His Ile Thr Ala Thr Gln Ala
1               5

<210> SEQ ID NO 218
<211> LENGTH: 9
<212> TYPE: PRT
<213> ORGANISM: Artificial
<220> FEATURE:
<223> OTHER INFORMATION: CLP-2950

<400> SEQUENCE: 218

Ile Thr Ala Thr Gln Ala Ile Arg Ile
1               5
```

TUMOR ANTIGENS BFA4 AND BCY1 FOR PREVENTION AND / OR TREATMENT OF CANCER

RELATED APPLICATIONS

This application claims priority to U.S. Ser. Nos. 60/394,346 filed Jul. 3, 2002; 60/394,503 filed Jul. 9, 2002; 60/411,833 filed Sep. 18, 2002; and, 60/445,342 filed Feb. 6, 2003, all of which being hereby incorporated by reference.

FIELD OF THE INVENTION

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

BACKGROUND OF THE INVENTION

There has been tremendous increase in last few years in the development of cancer vaccines with Tumour-associated antigens (TAAs) due to the great advances in identification of molecules based on the expression profiling on primary tumours and normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offringa et al, 2000). The TAAs are antigens expressed or over-expressed by tumour cells and could be specific to one or several tumours for example CEA antigen is expressed in colorectal, breast and lung cancers. Sgroi et al (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines such as IFN-γ, IL2, or GM-CSF, among others. Co-expression of a TAA and a cytokine or a co-stimulatory molecule can develop effective therapeutic vaccine (Hodge et al, 95, Bronte et al, 1995, Chamberlain et al, 1996).

There is a need in the art for reagents and methodologies useful in stimulating an immune response to prevent or treat cancers. The present invention provides such reagents and methodologies which overcome many of the difficulties encountered by others in attempting to treat cancer.

SUMMARY OF THE INVENTION

The present invention provides an immunogenic target for administration to a patient to prevent and/or treat cancer. In particular, the immunogenic target is a tumor antigen ("TA") and/or an angiogenesis-associated antigen ("AA"). In one embodiment, the immunogenic target is encoded by SEQ ID NO.: 1 or 3 or has the amino acid sequence of SEQ ID NO.: 2 or 4. In certain embodiments, the TA and/or AA are administered to a patient as a nucleic acid contained within a plasmid or other delivery vector, such as a recombinant virus. The TA and/or AA may also be administered in combination with an immune stimulator, such as a co-stimulatory molecule or adjuvant.

BRIEF DESCRIPTION OF THE DRAWINGS

FIG. 1. BFA4 cDNA sequence.
FIG. 2. BFA4 amino acid sequence.
FIG. 3. BCY1 nucleotide (A-C) and amino acid (D) sequences.

DETAILED DESCRIPTION

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule (such as a polypeptide) or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increased cellular response (i.e., increased T cells). An antigen that produces an immune response may alternatively be referred to as being immunogenic or as an immunogen. In describing the present invention, a TA may be referred to as an "immunogenic target".

TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host to whom the TA has been administered. Suitable TAs include, for example, gp100 (Cox et al., *Science*, 264:716-719 (1994)), MART-1/Melan A (Kawakami et al., *J. Exp. Med.*, 180:347-352 (1994)), gp75 (TRP-1) (Wang et al., *J. Exp. Med.*, 186:1131-1140 (1996)), tyrosinase (Wolfel et al., *Eur. J Immunol.*, 24:759-764 (1994); WO 200175117; WO 200175016; WO 200175007), NY-ESO-1 (WO 98/14464; WO 99/18206), melanoma proteoglycan (Hellstrom et al., *J. Immunol.*, 130:1467-1472 (1983)), MAGE family antigens (i.e., MAGE-1, 2,3,4,6,12, 51; Van der Bruggen et al., *Science*, 254:1643-1647 (1991); U.S. Pat. No. 6,235,525; CN 1319611), BAGE family antigens (Boel et al., *Immunity*, 2:167-175 (1995)), GAGE family antigens (i.e., GAGE-1,2; Van den Eynde et al., *J. Exp. Med.,* 182:689-698 (1995); U.S. Pat. No. 6,013,765), RAGE family antigens (i.e., RAGE-1; Gaugler et at., *Immunogenetics,* 44:323-330 (1996); U.S. Pat. No. 5,939,526), N-acetylglucosaminyltransferase-V (Guilloux et at., *J. Exp. Med.,* 183:1173-1183 (1996)), p15 (Robbins et al., *J. Immunol.* 154:5944-5950 (1995)), β-catenin (Robbins et al., *J. Exp. Med.,* 183:1185-1192 (1996)), MUM-1 (Coulie et al., *Proc. Natl. Acad. Sci.* USA, 92:7976-7980 (1995)), cyclin dependent kinase-4 (CDK4) (Wolfel et al., *Science,* 269:1281-1284 (1995)), p21-ras (Fossum et at., *Int. J Cancer,* 56:40-45 (1994)), BCR-abl (Bocchia et al., *Blood,* 85:2680-2684 (1995)), p53 (Theobald et al., *Proc. Natl. Acad. Sci.* USA, 92:11993-11997 (1995)), p185 HER2/ neu (erb-B1; Fisk et al., *J. Exp. Med.,* 181:2109-2117 (1995)), epidermal growth factor receptor (EGFR) (Harris et al., *Breast Cancer Res. Treat,* 29:1-2 (1994)), carcinoembryonic antigens (CEA) (Kwong et al., *J. Natl. Cancer Inst.,* 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., *J. Immunol.,* 151:1654-1662 (1993)); EBNA gene products of EBV (i.e., EBNA-1; Rickinson et al., *Cancer Surveys,* 13:53-80 (1992)); E7, E6 proteins of human papillomavirus (Ressing et al., *J. Immunol,* 154:5934-5943 (1995)); prostate specific antigen (PSA; Xue et al., *The Prostate,* 30:73-78 (1997)); prostate specific membrane antigen (PSMA; Israeli, et al., *Cancer Res.,* 54:1807-1811 (1994)); idiotypic epitopes or antigens, for example, immunoglobulin idiotypes or T cell receptor idiotypes (Chen et al., *J. Immunol.,* 153:4775-4787 (1994)); KSA (U.S. Pat. No. 5,348,887), kinesin 2 (Dietz, et al. Biochem Biophys Res Commun 2000 Sep. 7;275(3):731-8), HIP-55, TGFβ-1 antiapoptotic factor (Toomey, et al. Br J Biomed Sci 2001;58(3): 177-83), tumor protein D52 (Bryne J. A., et al., Genomics, 35:523-532 (1996)), H1FT, NY-BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in *Cancer Vaccines 2000,* Cancer Research Institute, New York, N.Y.), BFA4 (SEQ ID NOS.: 26 and 27), or BCY1 (SEQ ID NOS.: 28 and 29), including "wild-type" (i.e., normally encoded by the genome, naturally-occurring), modified, and mutated versions as well as other fragments and derivatives thereof. Any of these TAs may be utilized alone or in combination with one another in a co-immunization protocol.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. Where the cancer is cancer, it is preferred that that the AA be found within or near blood vessels that supply a tumor. Immunization of a patient against an AA preferably results in an anti-AA immune response whereby angiogenic processes that occur near or within tumors are prevented and/or inhibited.

Exemplary AAs include, for example, vascular endothelial growth factor (i.e., VEGF; Bemardini, et al. *J. Urol.,* 2001, 166(4): 1275-9; Stames, et al. *J. Thorac. Cardiovasc. Surg.,* 2001, 122(3): 518-23; Dias, et al. *Blood,* 2002, 99: 2179-2184), the VEGF receptor (i.e., VEGF-R, flk-1/KDR; Starnes, et al. *J. Thorac. Cardiovasc. Surg.,* 2001, 122(3): 518-23), EPH receptors (i.e., EPHA2; Gerety, et al. 1999, *Cell,* 4: 403-414), epidermal growth factor receptor (i.e., EGFR; Ciardeillo, et al. Clin. Cancer Res., 2001, 7(10): 2958-70), basic fibroblast growth factor (i.e., bFGF; Davidson, et al. Clin. Exp. Metastasis 2000,18(6): 501-7; Poon, et al. Am J. Surg., 2001, 182(3):298-304), platelet-derived cell growth factor (i.e., PDGF-B), platelet-derived endothelial cell growth factor (PD-ECGF; Hong, et al. J. Mol. Med., 2001, 8(2):141-8), transforming growth factors (i.e., TGF-α; Hong, et al. J. Mol. Med., 2001, 8(2):141-8), endoglin, (Balza, et al. *Int. J. Cancer,* 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Ophthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. Cancer Res., 2001, 61(16):6050-4), cyclin-dependent kinases (CDKs; Drug Resist. Updat. 2000, 3(2):83-88), microtubules (Timar, et al. 2001. *Path. Oncol. Res.,* 7(2): 85-94), heat shock proteins (i.e., HSP90 (Timar, supra)), heparin-binding factors (i.e., heparinase; Gohji, et al. Int. J. Cancer, 2001, 95(5):295-301), synthases (i.e., ATP synthase, thymidilate synthase), collagen receptors, integrins (i.e., αvβ3, αvβ5, α1β1, α2β1, α5β1), or surface proteolglycan NG2, among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

In certain embodiments, a nucleic acid molecule encoding an immunogenic target is utilized. The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not be linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The identity of two or more nucleic acid or polypeptide molecules is determined by comparing the sequences. As known in the art, "identity" means the degree of sequence relatedness between nucleic acid molecules or polypeptides as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the related sequence to hybridize to the nucleic acid sequence or isolated nucleic acid molecule. In defining such sequences, the term "highly stringent conditions" and "moderately stringent conditions" refer to procedures that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH.

In preferred embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a trascriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound such as tetracycline). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include the CMV promoter (i.e., the CMV-immediate early promoter); promoters from eukaryotic genes (i.e., the estrogen-inducible chicken ovalbumin gene, the interferon genes, the glucocorticoid-inducible tyrosine aminotransferase gene, and the thymidine kinase gene); and the major early and late adenovirus gene promoters; the SV40 early promoter region (Benoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. US.A.,* 80:21-25). Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.* 50:399-409

(1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-76); the alpha-feto-protein gene control region in liver (Krumlauf et al., 1985, *Mol. Cell. Biol.,* 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 February;23(1):154-8; Siders, et al. Cancer Gene Ther 1998 September-October;5(5):281-91), among others. Inducible promoters that are activated in the presence of a certain compound or condition such as light, heat, radiation, tetracycline, or heat shock proteins, for example, may also be utilized (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a cell, and a cell has been transfected when the exogenous DNA has been introduced inside the cell membrane. A number of transfection techniques are well known in the art (i.e., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The present invention further provides isolated immunogenic targets in polypeptide form. A polypeptide is considered isolated where it: (1) has been separated from at least about 50 percent of polynucleotides, lipids, carbohydrates, or other materials with which it is naturally found when isolated from the source cell; (2) is not linked (by covalent or noncovalent interaction) to all or a portion of a polypeptide to which the "isolated polypeptide" is linked in nature; (3) is operably linked (by covalent or noncovalent interaction) to a polypeptide with which it is not linked in nature; or, (4) does not occur in nature. Preferably, the isolated polypeptide is substantially free from any other contaminating polypeptides or other contaminants that are found in its natural environment that would interfere with its therapeutic, diagnostic, prophylactic or research use.

Immunogenic target polypeptides may be mature polypeptides, as defined herein, and may or may not have an amino terminal methionine residue, depending on the method by which they are prepared. Further contemplated are related polypeptides such as, for example, fragments, variants (i.e., allelic, splice), orthologs, homologues, and derivatives, for example, that possess at least one characteristic or activity (i.e., activity, antigenicity) of the immunogenic target. Also related are peptides, which refers to a series of contiguous amino acid residues having a sequence corresponding to at least a portion of the polypeptide from which its sequence is derived. In preferred embodiments, the peptide comprises about 5-10 amino acids, 10-15 amino acids, 15-20 amino acids, 20-30 amino acids, or 30-50 amino acids. In a more preferred embodiment, a peptide comprises 9-12 amino acids, suitable for presentation upon Class I MHC molecules, for example.

A fragment of a nucleic acid or polypeptide comprises a truncation of the sequence (i.e., nucleic acid or polypeptide) at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 10 amino acids, 20 amino acids, 30 amino acids, 40 amino acids, 50 amino acids, or more. The polypeptide fragments so produced will comprise about 10 amino acids, 25 amino acids, 30 amino acids, 40 amino acids, 50 amino acids, 60 amino acids, 70 amino acids, or more. Such polypeptide fragments may optionally comprise an amino terminal methionine residue. It will be appreciated that such fragments can be used, for example, to generate antibodies or cellular immune responses to immunogenic target polypeptides.

A variant is a sequence having one or more sequence substitutions, deletions, and/or additions as compared to the subject sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

An allelic variant is one of several possible naturally-occurring alternate forms of a gene occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target polypeptide may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particlar, does not result in decreased immunogenicity. Suitable conservative amino acid substitutions are shown in Table I.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptide using well-known techniques. For identifying suitable areas of the molecule that may be changed without destroying biological activity (i.e., MHC binding, immunogenicity), one skilled in the art may target areas not believed to be important for that activity. For example, when similar polypeptides with similar activities from the same species or from other species are known, one skilled in the art may compare the amino acid sequence of a polypeptide to such similar polypeptides. By performing such analyses, one can identify residues and portions of the molecules that are conserved among similar polypeptides. It will be appreciated that changes in areas of the molecule that are not conserved relative to such similar polypeptides would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for structure may be subject to conservative amino acid substitutions without destroying the biological activity or without adversely affecting the polypeptide structure.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the isolated polypeptides of the current invention include fusion polypeptide segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. These sequences, referred to as tranduction or transcytosis sequences, include sequences derived from HIV tat (see Kim et al. 1997 J. Immunol. 159:1666), *Drosophila antennapedia* (see Schutze-Redelmeier et al. 1996 J. Immunol. 157:650), or human period-1 protein (hPER1; in particular, SRRHHCRSKAKRSRHH).

In addition, the polypeptide or variant thereof may be fused to a homologous polypeptide to form a homodimer or to a heterologous polypeptide to form a heterodimer. Heterologous peptides and polypeptides include, but are not limited to: an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide or variant thereof.

In certain embodiments, it may be advantageous to combine a nucleic acid sequence encoding an immunogenic target, polypeptide, or derivative thereof with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.*, 156(8): 2700-9) and B7.2 (CD86; Ellis, et al. *J. Immunol.*, 156(8): 2700-9); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27 ligand; Couderc, et al. *Cancer Gene Ther.*, 5(3): 163-75). CD154 (CD40 ligand or "CD40L"; Gurunathan, et al. *J. Immunol.*, 1998, 161: 4563-4571; Sine, et al. *Hum. Gene Ther.*, 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August;2(4):243-9; Rao, et al. *J. Immunol.* 156: 3357-3365 (1996)), IL-15 (Xin, et al. *Vaccine,* 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), or interferons such as IFN-α or INF-γ. Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor, immunity (Biragyn, et al. *Nature Biotech.* 1999, 17: 253-258). The chemokines CCL3 (MIP-1α) and CCL5 (RANTES) (Boyer, et al. *Vaccine,* 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity,* 1996, 14: 145-155; Sutmuller, et al. *J. Exp. Med.,* 2001, 194: 823-832), anti-CD25 (Sutmuller, supra), anti-CD4 (Matsui, et al. *J. Immunol.,* 1999, 163: 184-193), the fusion protein IL13Ra2-Fc (Terabe, et al. *Nature Immunol.,* 2000, 1: 515-520), and combinations thereof (i.e., anti-CTLA-4 and anti-CD25, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol.,* 158: 3947-3958 (1997); Iwasaki, et al. *J. Immunol.* 158: 4591-4601 (1997)), IL-12+GM-CSF+TNF-α (Ahlers, et al. *Int Immunol.* 13: 897-908 (2001)), CD80+IL-12 (Fruend, et al. *Int. J Cancer,* 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J Virol.* 75: 4947-4951), in vivo electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra; Cho, et al. J. Immunol. 168(10): 4907-13), sequences for targeting of the endocytic or ubiquitin-processing pathways (Thomson, et al. 1998. *J. Virol.* 72: 2246-2252; Velders, et al. 2001. *J. Immunol.* 166: 5366-5373), Marek's disease virus type 1 VP22 sequences (J. Virol. 76(6):2676-82, 2002), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), and the use of mucosal delivery vectors such as Salmonella (Darji, et al. 1997. *Cell,* 91: 765-775; Woo, et al. 2001. *Vaccine,* 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. Oncogene 2000 Dec. 27;19(56):6566-73). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utlized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the immunogenic target vaccines (see, for example, Timar, et al. 2001. *Pathology Oncol. Res.,* 7(2): 85-94). Such agents include, for example, physiological agents such as growth factors (i.e., ANG-2, NK1,2,4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HU177, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, *Nature Med.,* 8: 128-135), CEP-7055 (available from Cephalon, Inc.), flavone acetic acid, Bay 12-9566 (Bayer Corp.), AG3340 (Agouron, Inc.), CGS 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acteyl-L-cysteine), combretastatin A-4 (Oxigene), Eph receptor blocking agents (*Nature,* 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, Clostridium novyi was modified to eliminate a toxin gene carried on a phage episome and administered to mice with colorectal tumors (Dang, et al. *P.N.A.S. USA,* 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include T2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp. Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science*, 252 (5004): 431-4; Crystal, R., et al., 1994, *Nat. Genet.*, 8 (1): 42-51), the study eukaryotic gene expression (Levrero, M., et al., 1991, *Gene*, 101 (2): 195-202), vaccine development (Graham, F. and Prevec, L., 1992, *Biotechnology*, 20: 363-90), and in animal models (Stratford-Perricaudet, L., et al., 1992, *Bone Marrow Transplant.*, 9 (Suppl. 1): 151-2; Rich, D., et al., 1993, *Hum. Gene Ther.*, 4 (4): 461-76). Experimental routes for administrating recombinant Ad to different tissues in vivo have included intratracheal instillation (Rosenfeld, M., et al., 1992, *Cell*, 68 (1): 143-55) injection into muscle (Quantin, B., et al., 1992, *Proc. Natl. Acad. Sci. U.S.A.*, 89 (7): 2581-4), peripheral intravenous injection (Herz, J., and Gerard, R., 1993, *Proc. Natl. Acad. Sci. U.S.A.*, 90 (7): 2812-6) and stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Poxvirus is another useful expression vector (Smith, et al. 1983, *Gene*, 25 (1): 21-8; Moss, et al, 1992, *Biotechnology*, 20: 345-62; Moss, et al, 1992, *Curr. Top. Microbiol. Immunol.*, 158: 25-38; Moss, et al. 1991. *Science*, 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (14L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the American Type Culture Collection (ATCC), P.O. Box 1549, 10801 University Boulevard, Manassas, Va 20110-2209. USA under the terms of the Budapest Treaty, as accession numbers VR-2559, VR-2558, VR-2557, VR-2556, ATCC-97913, ATCC-97912, and ATCC-97914, respectively, all deposits made on Mar. 6, 1996.

ALVAC-based recombinant viruses (i.e., ALVAC-1 and ALVAC-2) are also suitable for use in practicing the present invention (see, for example, U.S. Pat. No. 5,756,103). ALVAC(2)is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833, 975). ALVAC was deposited under the terms of the Budapest Treaty with the American Type Culture Collection (ATCC), P.O. Box 1549, 10801 University Boulevard, Manassas, Va. 20110-2209, USA, as ATCC accession number VR-2547, on November 14, 1996.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the American Type Culture Collection (ATCC). P.O. Box 1549, 10801 University Boulevard, Manassas, Va. 20110-2209, USA, as accession number 2553, on Feb. 6, 1997.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBachl, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA cloning® kit, PCR2.1® plasmid derivatives, Invitrogen, Carlsbad, Calif.). Bacterial vectors may also be used with the current invention. These vectors include, for example, Shigella, Salmonella, *Vibrio cholerae*, Lactobacillus, *Bacille calmette guérin* (BCG), and Streptococcus (see for example, WO 88/6626; WO 90/0594; WO 91/13157; WO 92/1796; and WO 92/21376). Many other non-viral plasmid expression vectors and systems are known in the art and could be used with the current invention.

such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table II below:

TABLE II

Types of Immunologic Adjuvants

| Type of Adjuvant | General Examples | Specific Examples/References |
|---|---|---|
| Gel-type | Aluminum hydroxide/phosphate ("alum adjuvants") | (Aggerbeck and Heron, 1995) |
| | Calcium phosphate | (Relyveld, 1986) |
| Microbial | Muramyl dipeptide (MDP) | (Chedid et al., 1986) |
| | Bacterial exotoxins | Cholera toxin (CT), *E. coli* labile toxin (LT)(Freytag and Clements, 1999) |
| | Endotoxin-based adjuvants | Monophosphoryl lipid A (MPL) (Ulrich and Myers, 1995) |
| | Other bacterial | CpG oligonucleotides (Corral and Petray, 2000), BCG sequences (Krieg, et al. Nature, 374: 576), tetanus toxoid (Rice, et al. J. Immunol., 2001, 167: 1558–1565) |
| Particulate | Biodegradable Polymer microspheres | (Gupta et al., 1998) |
| | Immunostimulatory complexes (ISCOMs) | (Morein and Bengtsson, 1999) |
| | Liposomes | (Wassef et al., 1994) |
| Oil-emulsion and surfactant-based adjuvants | Freund's incomplete adjuvant | (Jensen et al., 1998) |
| | Microfluidized emulsions | MF59 (Ott et al., 1995) SAF (Allison and Byars, 1992) (Allison, 1999) |
| | Saponins | QS-21 (Kensil, 1996) |
| Synthetic | Muramyl peptide derivatives | Murabutide (Lederer, 1986) Threony-MDP (Allison, 1997) |
| | Nonionic block copolymers | L121 (Allison, 1999) |
| | Polyphosphazene (PCPP) | (Payne et al., 1995) |
| | Synthetic polynucleotides | Poly A:U, Poly I:C (Johnson, 1994) |
| | Thalidomide derivatives | CC-4047/ACTIMID (J. Immunol., 168(10): 4914–9) |

Suitable nucleic acid delivery techniques include DNA-ligand complexes, adenovirus-ligand-DNA complexes, direct injection of DNA, CaPO$_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, The immunogenic targets of the present invention may also be used to generate antibodies for use in screening assays or for immunotherapy. Other uses would be apparent to one of skill in the art. The term "antibody" includes antibody fragments, as are known in the art, including Fab, Fab$_2$, single chain antibodies (Fv for example), humanized antibodies, chimeric antibodies, human antibodies, produced by several methods as are known in the art. Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). The antibodies or derivatives therefrom may also be conjugated to therapeutic moieties such as cytotoxic drugs or toxins, or active fragments thereof such as diptheria A chain, exotoxin A chain, ricin A chain, abrin A chain, curcin, crotin, phenomycin, enomycin, among others. Cytotoxic agents may also include radiochemicals. Antibodies and their derivatives may be incorporated into compositions of the invention for use in vitro or in vivo.

Nucleic acids, proteins, or derivatives thereof representing an immunogenic target may be used in assays to determine the presence of a disease state in a patient, to predict prognosis, or to determine the effectiveness of a chemotherapeutic or other treatment regimen. Expression profiles, performed as is known in the art, may be used to determine the relative level of expression of the immunogenic target. The level of expression may then be correlated with base levels to determine whether a particular disease is present within the patient, the patient's prognosis, or whether a particular treatment regimen is effective. For example, if the patient is being treated with a particular chemotherapeutic regimen, an decreased level of expression of an immunogenic target in the patient's tissues (i.e., in peripheral blood) may indicate the regimen is decreasing the cancer load in that host. Similarly, if the level of expresssion is increasing, another therapeutic modality may need to be utilized. In one embodiment, nucleic acid probes corresponding to a nucleic acid encoding an immunogenic target may be attached to a biochip, as is known in the art, for the detection and quantification of expression in the host.

It is also possible to use nucleic acids, proteins, derivatives therefrom, or antibodies thereto as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parenterally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxviral vector may be administered as a composition comprising $1 \times 10^6$ infectious particles per dose. Thus, the dosage regimen may vary widely, but can be determined routinely using standard methods.

A prime-boost regimen may also be utilized (WO 01/30382 A1) in which the targeted immunogen is initially administered in a priming step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host. Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 1988), HER-2 (Fendly et al., 1990), the melanoma-associated antigens (MAGE-1; MAGE-2) (van der Bruggen et al., 1991), p97 (Hu et al., 1988), melanoma-associated antigen E (WO 99/30737) and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other antineoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

BFA4 Tumor Antigen

The BFA4 sequence was found to be the "trichorhinophalangeal syndrome 1" (TRPS-1) gene (Genebank ID #6684533; Momeniet et al, Nature Genetics, 24(1), 71-74, 2000), a known transcription factor with no function attributed previously in any form of cancer. The BFA4 cDNA sequence is shown in FIG. 1 and the deduced amino acid sequence is shown in FIG. 2.

A. BFA4 Peptides and Polyclonal Antisera

For monitoring purposes, rabbit anti-BFA4 polyclonal antibodies were generated. Six peptides (22-mers) were designed and synthesized to elicit antibody response to BFA4, as shown below:

| CLP 2589 | MVRKKNPPLRNVASEGEGQILE | BFA4 (1-22) |
| CLP 2590 | SPKATEETGQAQSGQANCQGLS | BFA4 (157-178) |
| CLP 2591 | VAKPSEKNSNKSIPALQSSDSG | BFA4 (371-392) |
| CLP 2592 | NHLQGSDGQQSVKESKEHSCTK | BFA4 (649-670) |
| CLP 2593 | NGEQIIRRRTRKRLNPEALQAE | BFA4 (940-961) |
| CLP 2594 | ANGASKEKTKAPPNVKNEGPLNV | BFA4 (1178-1199) |

Rabbits were immunized with the peptides, serum was isolated, and the following antibody titers were observed:

| Rabbit # | Peptide | Titer (Bleed 2) | Titer (Final Bleed) |
|---|---|---|---|
| 1, 2 | CLP2589 | 800000, 1600000 | 2560000, 2560000 |
| 3, 4 | CLP2590 | 12800, 6400 | 40000, 40000 |
| 5, 6 | CLP2591 | 400000, 400000 | 320000, 320000 |
| 7, 8 | CLP2592 | 25600, 12800 | 80000, 40000 |
| 9, 10 | CLP2593 | 3200000, 51200 | 2560000, 160000 |
| 11, 12 | CLP2594 | 409600, 409600 | 320000, 320000 |

These peptides were also modified by coupling with KLH peptides to enhance immune responses as shown below:

```
BFA4 (1-22)      KLH-MVRKKNPPLRNVASEGEG     (CLP-2589)
                 QILE

BFA4 (157-178)   KLH-SPKATEETGQAQSGQANC     (CLP-2590)
                 QGLS

BFA4 (371-392)   KLH-VAKPSEKNSNKSIPALQS     (CLP-2591)
                 SDSG

BFA4 (649-670)   KLH-NHLQGSDGQQSVKESKEH     (CLP-2592)
                 SCTK

BFA4 (940-961)   KLH-NGEQIIRRRTRKRLNPEA     (CLP-2593)
                 LQAE

BFA4 (1178-1200) KLH-ANGASKEKTKAPPNVKNE     (CLP-2594)
                 GPLNV
```

The pcDNA3.2BFA4 (3.6 mg) was also used for DNA immunization to generate polyclonal sera in chickens.

B. Cloning of BFA4

Complete cDNA sequence for BFA4 is ~10 kb and gene is expressed in BT474 ductal carcinoma cells. Primers 7717 (forward primer) and 7723 (reverse primer) were designed to amplify full-length BFA4 gene by amplification of 4 kb, 7 kb or 10 kb products by RT-PCR.

Primer 7717: BFA4-BamH1/F1 (5' end forward) with Kozak:
 5' CGGGATCCACCATGGTCCGGAAAAAGAACCCC 3'(BamHI for DNA3.1, MP76)

Primer 7723: BFA4-BamHI/R1 (3' end reverse 4 kb):
 5' CGGGATCCCTCTTTAGGTTTTCCATTTTTTTCCAC 3' (BamHI for DNA3.1, MP76)

Ten mg of total RNA isolated and frozen in different batches from BT-474 cells using Trizol as indicated by the manufacturer (Gibco BRL) was used in RT-PCR to amplify the BFA4 gene. RT-PCR conditions were optimized using Taq Platinum High Fidelity enzyme, OPC (Oligo Purification Cartridge; Applied Biosystems) purified primers and purified total RNA/polyA mRNA (BT 474 cells). Optimization resulted in a 4.0 kb fragment as a single band.

To re-amplify the BFA4 sequence, mRNA was treated with DNase per manufacturers' instructions (Gibco BRL). The 4 kb DNA was reamplified using PCR using primers 7717 and 7723 primers (10 pmole/microliter) and Taq Platinum High Fidelity polymerase (GIBCO BRL) enzyme. Thermocycler conditions for both sets of reactions were as under: 94° C. (2 min), followed by 30 cycles of 94° C. (30 sec), 52° C. (30 sec), 67° C. (4 min) and 67° C. (5 min) and finally 40° C. for 10 min. Three BFA4 clones were identified after pCR2.1/TOPO-TA cloning.

Several mutations were identified during analysis of the BFA4 sequence. To correct these sequences, the BamHI/XhoI fragment (5') of the BFA4 gene from clone JB-3552-1-2 (pCR2.1/TOPO/BFA4) was exchanged with the XhoI/BamHI fragment (3') of the BFA4 gene from clone JB-3552-1-4 (pCR2.1/TOPO/BFA4). This recombed fragment was then ligated into pMCS5 BamHI/CAP. Clone JB-3624-1-5 was generated and found to contain the correct sequence.

Nucleotide 344 of the isolated BFA4 clone was different from the reported sequence (C in BFA4, T in TRPS-1). The change resulted in a phe to ser amino acid change. To change this sequence to the reported sequence, the EcoRI/BglII fragment (5') of the BFA4 gene from clone JB-3552-1-2 (pCR2.1/TOPO/BFA4) was subcloned into pUC8:2 to generate clone JB-3631-2. This clone was used as a template for Quickchange (Stratagene) mutagenesis to change amino acid 115 of the BFA4 protein from a serine to a phenylalanine as in the TRPS1 protein. The selected clone was JB-3648-2-3. Mutagenesis was also repeated with pMCS5 BFA4 (BT474) as a template for Quickchange (Stratagene) mutagenesis to change amino acid 115 of the BFA4 protein from a serine to a phenylalanine as in the TRPSI protein. Several clones were found to be correct by DNA sequencing and one of the clones (JB-3685-1-18) was used for further subcloning.

JB-3685-1-18 was then used to subclone the BFA4 coding sequence into the BamHI sites of four different expression vectors: 1) the poxviral (NYVAC) vector pSD554VC (CO-PAK/H6; JB-3707-1-7); 2) pcDNA3.1/Zeo (+) (JB-3707-3-2); 3) pCAMycHis (JB-3707-5-1); and, 4) Semiliki Forest virus alphaviral replicon vector pMP76 (JB-3735-1-23). The BFA4 coding sequence within JB-3707-1-7, JB-3707-5-1, and JB-3735-1-23 was confirmed by DNA sequencing.

A stop codon was introduced near the end of the cloned sequence in the pcDNA3.1/Zeo/BFA4 construct (JB-3707-3-2). A unique EcoRl site was opened and filled in to introduce a stop codon in-frame with BFA4 coding sequence. Several putative clones were identified by the loss of EcoRl site, however three clones (JB-3756-1-2; JB-3756-3-1; and JB-3756-4-1) were sequenced. All three were found to be correct in the area of the fill-in. Clone JB-3756-3-1 identified as having the correct sequence and orientation.

Myc and myc/his tags (Evans et al, 1985) were introduced using oligonucleotides, which were annealed and ligated into the pcDNA3.1/Zeo/BFA4 construct (JB-3707-3-2) at the EcoRI/EcoRV sites. Several clones were obtained for these constructs. Three clones having the correct sequences and orientations were obtained: 1) PcDNA3.1/Zeo/BFA4/myc-tag (JB-3773-1-2); 2) PcDNA3.1/Zeo/BFA4/mychis-tag (JB-3773-2-1); and, 3) PcDNA3.1/Zeo/BFA4/mychis-tag (JB-3773-2-2).

C. Expression of BFA4

1. Expression From Poxviral Vectors

The pSD554VC (COPAK/H6; JB-3707-1-7) vector was used to generate NYVAC-BFA4 virus. In vitro recombination was performed with plasmid COPAK/H6/BFA4 and NYVAC in RK13/CEF cells. NYVAC-BFA4 (vP2033-NYVAC-RK13) was generated and amplified to P3 level after completion of three enrichments with final stock concentrations of $1.12 \times 10^9$/ml (10 ml). Vero cells were infected with NYVAC-BFA4 at an M.O.I. of 0.5 pfu/cell. Lysates and media were harvested 24 h post-infection to confirm expression of BFA4 protein. One-twentieth of the concentrated media and 1/40 of the lysate were loaded onto a western blot and incubated with rabbit antisera against the BFA4 peptides CLP 2589, 2591, 2598 and 2594 (see above for peptide sequences and preparation of anti-BFA4 antisera). An approximate 120 kD band was detected in both the lysate and the concentrated media of NYVAC-BFA4-infected Vero cells which was not evident in either Vero control cells ("mock-infected"), Vero cells infected with the parental NYVAC virus, or concentrated media.

2. Expression From pcDNA3.1-based Vectors

Transient transfection studies were performed to verify expression of BFA4 from the pcDNA-based vectors and to analyze quality of polyclonal sera raised against BFA4 peptides. The following constructs were used to study expression of BFA4 gene: pcDNA 3.1 zeoR/BFA4, pMP76/BFA4, pcDNA 3.1 zeor/BFA4/Myc tag and pcDNA 3.1 zeoR/BFA4/MycHis tag. BFA4 expression plasmids (5 µg and 10 µg) were co-transfected with pGL3 Luciferase (1 □g) (Promega) with the Gene porter reagent (Gene Therapy Systems) as the transfection reagent. At 48 h post-transfection, whole cell extract was prepared by scraping cells in cell lysis reagent (200 µl) and 1 cycle of freeze-thaw (−20° C. freeze, 37° C. thaw). Transfection efficiency was quantitated by analyzing expression of the luciferase reporter gene by measuring Relative Luciferase Units (RLU) in duplicate. Similar RLU values were obtained in the samples co-transfected with luciferase construct in the presence and absence of BFA4 expression vectors. There was no significant difference observed in toxicity or RLU values with differential amount (5 µg and 10 µg) of BFA4 expression vectors. Preliminary western blot analysis using alkaline phosphatase system with the CHOKI cell extracts (pCDNA3.1 /zeo/BFA4/MycHisTag) and an anti-BFA4 polyclonal antisera, revealed a band at approximately 120 kDa band in extracts of BFA4 vector-transfected cells.

A stable transfection study was initiated to obtain stable clones of BFA4 expressing COS A2 cells. These cells are useful for in vitro stimulation assays. pcDNA 3.1 zeo$^R$/BFA4 (2.5 µg and 20 µg), and pcDNA 3.1 zeo$^R$/BFA4/MycHis tag (2.5 µg) were used to study expression of BFA4). pGL3 Luciferase (2.5 µg) was used as a control vector to monitor transfection efficiency. The Gene porter reagent was used to facilitate transfection of DNA vectors. After 48 h post-transfection, whole cell extract were prepared by scraping cells in the cell lysis reagent (200 µl) and 1 cycle of freeze-thaw at −20° C./37° C. for first experiment. Transfected cells obtained from the second experiment were trypsinized, frozen stock established and cells were plated in increasing concentrations of Zeocin (0, 250, 500, 750 and 1000 µg/ml). Non-transfected CosA2cells survived at 60-80% confluency for three weeks at 100 µg/ml (Zeocin) and 10% confluency at 250 µg/ml (Zeocin). However, after three weeks, at higher drug concentration (500-1000 µg/ml), live cells were not observed in the plates containing non-transfected cells and high Zeocin concentration (500-1000 µg/ml).

Several Zeocin-resistant clones growing in differential drug concentrations (Zeocin-250, 500, 750 and 1000 µg/ml) were picked from 10 cm plates after three weeks. These clones were further expanded in a 3.5 cm plate(s) in the presence of Zeocin at 500, 750 and 1000 µg/ml. Frozen lots of these clones were prepared and several clones from each pool (pcDNA 3.1 zeo$^R$/BFA4, and pcDNA 3.1 zeor/BFA4/MycHis tag) were expanded to T75 cm$^2$ flasks in the presence of Zeocin at 1 mg/ml. Five clones from each pool (pcDNA 3.1 zeo$^R$/BFA4, and pcDNA 3.1 zeo$^R$/BFA4/MycHis tag) were expanded to T75 cm$^2$ flasks in the presence of Zeocin at 1 mg/ml. Cells are maintained under Zeocin drug (1 mg/ml) selection. Six clones were used in BFA4 peptide-pulsed target experiment, and two clones were found to express BFA4 at a moderate level by immunological assays. The non-adherent cell lines K562A2 and EL4A2 were also transfected with these vectors to generate stable cell lines.

3. Prokaryotic Expression Vector

The BamHI-Xho-1 fragment (1.5 Kbp) fragment encoding N-terminal 54kDa BFDA4 from pCDNA3.1/BFA4 was cloned into pGEX4T1-6His (Veritas) plasmid. This vector contains the tac promoter followed by the N-terminal glutathione S-transferase (GST~26 kDa) and a hexahistidine tag to C terminus of the GST fusion protein.

The BFA4-N54 expression plasmid was transformed into BL21 cells and grown at 25° C. in antibiotic selection medium (2 L culture) to an OD (600 nm) and thereafter induced with 1 mM IPTG. GST-BFA4-N54 was found to be soluble protein. Clarified extract of the soluble fraction was adsorbed batchwise to glutathione-Sepharose 4B and eluted with 10 mM reduced glutathione. Fractions were analyzed after estimation of protein concentration and TCA precipitation. Specific polypeptide of Mr=85 kDa in the eluate was confirmed by SDS-PAGE. The recombinant protein was purified by gluathione-Sepharose was absorbed on a NiNTA column for further purification. The bound protein was eluted with 0.25M imidazole. The protein was dialyzed versus TBS containing 40% Glycerol, resulting in 4.5 mg GST-BFA4-N54-6 His (N terminus BFA4 protein) protein. Expression of BFA4 was confirmed using the rabbit anti-BFA4 polyclonal antibody by western blot.

D. Therapeutic Anti-BFA4 Immune Responses

1. BFA4 Peptides

In addition to genetic immunization vectors for BFA4, immunological reagents for BFA4 have been generated. A library of 100 nonamer peptides spanning the BFA4 gene product was synthesized. The peptides were chosen based on their potential ability to bind to HLA-A*0201. Table V lists 100 nonamer peptide epitopes for HLA-A*0201 from the BFA4 protein tested (see below):

| PEPTIDE DESIGNATION | SEQUENCE | POSITION IN PROTEIN |
|---|---|---|
| CLP-2421 | MVRKKNPPL | BFA4 (1-9)i" |
| CLP-2422 | KKNPPLRNV | BFA4 (4-12)i" |
| CLP-2423 | VASEGEGQI | BFA4 (12-20)i" |
| CLP-2424 | QILEPIGTE | BFA4 (19-27)i" |
| CLP-2425 | RNMLAFSFP | BFA4 (108-116)i" |
| CLP-2426 | NMLAFSFPA | BFA4 (109-117)i" |
| CLP-2427 | MLAFSFPAA | BFA4 (110-118)i" |
| CLP-2428 | FSFPAAGGV | BFA4 (113-121)i" |
| CLP-2429 | AAGGVCEPL | BFA4 (117-125)i" |
| CLP-2430 | SGQANCQGL | BFA4 (170-178)i" |
| CLP-2431 | ANCQGLSPV | BFA4 (172-180)i" |
| CLP-2432 | GLSPVSVAS | BFA4 (176-184)i" |
| CLP-2433 | SVASKNPQV | BFA4 (181-189)i" |
| CLP-2434 | RLNKSKTDL | BFA4 (196-204)i" |
| CLP-2435 | NDNPDPAPL | BFA4 (207-215)i" |
| CLP-2436 | DPAPLSPEL | BFA4 (211-219)i" |
| CLP-2437 | ELQDFKCNI | BFA4 (218-216)i" |
| CLP-2438 | GLHNRTRQD | BFA4 (249-257)i" |
| CLP-2439 | ELDSKILAL | BFA4 (259-267)i" |
| CLP-2440 | KILALHNMV | BFA4 (263-271)i" |
| CLP-2441 | ALHNMVQFS | BFA4 (266-284)i" |
| CLP-2442 | VNRSVFSGV | BFA4 (282-290)i" |
| CLP-2443 | FSGVLQDIN | BFA4 (287-295)i" |
| CLP-2444 | DINSSRPVL | BFA4 (293-301)i" |
| CLP-2445 | VLLNGTYDV | BFA4 (300-308)i" |

| PEPTIDE DESIGNATION | SEQUENCE | POSITION IN PROTEIN |
|---|---|---|
| CLP-2446 | FCNFTYMGN | BFA4 (337-345)i" |
| CLP-2447 | YMGNSSTEL | BFA4 (342-350)i" |
| CLP-2448 | FLQTHPNKI | BFA4 (354-362)i" |
| CLP-2449 | KASLPSSEV | BFA4 (363-371)i" |
| CLP-2450 | DLGKWQDKI | BFA4 (393-401)i" |
| CLP-2451 | VKAGDDTPV | BFA4 (403-411)i" |
| CLP-2452 | FSCESSSSL | BFA4 (441-449)i" |
| CLP-2453 | KLLEHYGKQ | BFA4 (450-458)i" |
| CLP-2454 | GLNPELNDK | BFA4 (466-474)i" |
| CLP-2455 | GSVINQNDL | BFA4 (478-486)i" |
| CLP-2456 | SVINQNDLA | BFA4 (479-487)i" |
| CLP-2457 | FCDFRYSKS | BFA4 (527-535)i" |
| CLP-2458 | SHGPDVIVV | BFA4 (535-543)i" |
| CLP-2459 | PLLRHYQQL | BFA4 (545-553)i" |
| CLP-2460 | GLCSPEKHL | BFA4 (570-578)i" |
| CLP-2461 | HLGEITYPF | BFA4 (577-585)i" |
| CLP-2462 | LGEITYPFA | BFA4 (578-586)i" |
| CLP-2463 | HCALLLLHL | BFA4 (594-602)i" |
| CLP-2464 | ALLLLHLSP | BFA4 (596-604)i" |
| CLP-2465 | LLLLHLSPG | BFA4 (597-605)i" |
| CLP-2466 | LLLHLSPGA | BFA4 (598-606)i" |
| CLP-2467 | LLHLSPGAA | BFA4 (599-607)i" |
| CLP-2468 | FTTPDVDVL | BFA4 (621-629)i" |
| CLP-2469 | TTPDVDVLL | BFA4 (622-630)i" |
| CLP-2470 | VLLFHYESV | BFA4 (628-636)i" |
| CLP-2471 | FITQVEEEI | BFA4 (673-681)i" |
| CLP-2472 | FTAADTQSL | BFA4 (699-707)i" |
| CLP-2473 | SLLEHFNTV | BFA4 (706-714)i" |
| CLP-2474 | STIKEEPKI | BFA4 (734-742)i" |
| CLP-2475 | KIDFRVYNL | BFA4 (741-749)i" |
| CLP-2476 | NLLTPDSKM | BFA4 (748-756)i" |
| CLP-2479 | VTWRGADIL | BFA4 (792-800)i" |
| CLP-2480 | ILRGSPSYT | BFA4 (799-807)i" |
| CLP-2481 | YTQASLGLL | BFA4 (806-814)i" |
| CLP-2482 | ASLGLLTPV | BFA4 (809-817)i" |
| CLP-2483 | GLLTPVSGT | BFA4 (812-820)i" |
| CLP-2484 | GTQEQTKTL | BFA4 (819-827)i" |
| CLP-2485 | KTLRDSPNV | BFA4 (825-833)i" |
| CLP-2486 | HLARPIYGL | BFA4 (837-845)i" |
| CLP-2487 | PIYGLAVET | BFA4 (841-849)i" |
| CLP-2488 | LAVETKGFL | BFA4 (845-853)i" |
| CLP-2489 | FLQGAPAGG | BFA4 (852-860)i" |
| CLP-2490 | AGGEKSGAL | BFA4 (858-866)i" |
| CLP-2491 | GALPQQYPA | BFA4 (864-872)i" |
| CLP-2492 | ALPQQYPAS | BFA4 (865-873)i" |
| CLP-2493 | FCANCLTTK | BFA4 (895-903)i" |
| CLP-2494 | ANGGYVCNA | BFA4 (911-919)i" |
| CLP-2495 | NACGLYQKL | BFA4 (918-926)i" |
| CLP-2496 | GLYQKLHST | BFA4 (921-929)i" |
| CLP-2497 | KLHSTPRPL | BFA4 (925-933)i" |
| CLP-2498 | STPRPLNII | BFA4 (928-936)i" |
| CLP-2499 | RLNPEALQA | BFA4 (952-960)i" |
| CLP-2500 | VLVSQTLDI | BFA4 (1020-1028)i" |
| CLP-2501 | DIHKRMQPL | BFA4 (1027-1035)i" |
| CLP-2502 | RMQPLHIQI | BFA4 (1031-1039)i" |
| CLP-2503 | YPLFGLPFV | BFA4 (1092-1100)i" |
| CLP-2504 | GLPFVHNDF | BFA4 (1096-1104)i" |
| CLP-2505 | FVHNDFQSE | BFA4 (1099-1107)i" |
| CLP-2506 | SVPGNPHYL | BFA4 (1120-1128)i" |
| CLP-2507 | GNPHYLSHV | BFA4 (1123-1131)i" |
| CLP-2508 | HYLSHVPGL | BFA4 (1126-1134)i" |
| CLP-2509 | YVPYPTFNL | BFA4 (1141-1149)i" |
| CLP-2510 | FNLPPHFSA | BFA4 (1147-1155)i" |
| CLP-2511 | NLPPHFSAV | BFA4 (1148-1156)i" |
| CLP-2512 | SAVGSDNDI | BFA4 (1154-1162)i" |
| CLP-2513 | KNEGPLNVV | BFA4 (1192-1200)i" |
| CLP-2514 | TKCVHCGIV | BFA4 (1215-1223)i" |
| CLP-2515 | CVHCGIVFL | BFA4 (1217-1225)i" |
| CLP-2516 | CGIVFLDEV | BFA4 (1220-1228)i" |
| CLP-2517 | FLDEVMYAL | BFA4 (1224-1232)i" |
| CLP-2518 | VMYALHMSC | BFA4 (1228-1236)i" |
| CLP-2519 | FQCSICQHL | BFA4 (1243-1251)i" |
| CLP-2520 | GLHRNNAQV | BFA4 (1265-1273)i" |

The peptide library was pooled into separate groups containing 7-10 different peptides for immunological testing as shown in Table VI (see below). In addition to a peptide library spanning BFA4, a recombinant protein spanning the N-terminal 300 amino acids (positions 1-300) has been synthesized and purified from E. coli.

| PEPTIDE GROUP | PEPTIDE NUMBER | SEQUENCE |
|---|---|---|
| 1 | CLP-2421 | MVRKKNPPL |
|   | CLP-2422 | KKNPPLRNV |
|   | CLP-2423 | VASEGEGQI |
|   | CLP-2424 | QILEPIGTE |
|   | CLP-2425 | RNMLAFSFP |
|   | CLP-2426 | NMLAFSFPA |
|   | CLP-2427 | MLAFSFPAA |
|   | CLP-2428 | FSFPAAGGV |
|   | CLP-2429 | AAGGVCEPL |
|   | CLP-2430 | SGQANCQGL |
| 2 | CLP-2431 | ANCQGLSPV |
|   | CLP-2432 | GLSPVSVAS |
|   | CLP-2433 | SVASKNPQV |
|   | CLP-2434 | RLNKSKTDL |
|   | CLP-2435 | NDNPDPAPL |
|   | CLP-2436 | DPAPLSPEL |
|   | CLP-2437 | ELQDFKCNI |
|   | CLP-2438 | GLHNRTRQD |
|   | CLP-2439 | ELDSKILAL |
|   | CLP-2440 | KILALHNMV |
| 3 | CLP-2441 | ALHNMVQFS |
|   | CLP-2442 | VNRSVFSGV |
|   | CLP-2443 | FSGVLQDIN |
|   | CLP-2444 | DINSSRPVL |
|   | CLP-2445 | VLLNGTYDV |
|   | CLP-2446 | FCNFTYMGN |
|   | CLP-2447 | YMGNSSTEL |
|   | CLP-2448 | FLQTHPNKI |
|   | CLP-2449 | KASLPSSEV |
|   | CLP-2450 | DLGKWQDKI |
| 4 | CLP-2451 | VKAGDDTPV |
|   | CLP-2452 | FSCESSSSL |
|   | CLP-2453 | KLLEHYGKQ |
|   | CLP-2454 | GLNPELNDK |
|   | CLP-2455 | GSVINQNDL |
|   | CLP-2456 | SVINQNDLA |
|   | CLP-2457 | FCDFRYSKS |

-continued

| PEPTIDE GROUP | PEPTIDE NUMBER | SEQUENCE |
|---|---|---|
|   | CLP-2458 | SHGPDVIVV |
|   | CLP-2459 | PLLRHYQQL |
|   | CLP-2460 | GLCSPEKHL |
| 5 | CLP-2461 | HLGEITYPF |
|   | CLP-2462 | LGEITYPFA |
|   | CLP-2463 | HCALLLLHL |
|   | CLP-2464 | ALLLLHLSP |
|   | CLP-2465 | LLLLHLSPG |
|   | CLP-2466 | LLLHLSPGA |
|   | CLP-2467 | LLHLSPGAA |
|   | CLP-2468 | FTTPDVDVL |
|   | CLP-2469 | TTPDVDVLL |
|   | CLP-2470 | VLLFHYESV |
| 6 | CLP-2471 | FITQVEEEI |
|   | CLP-2472 | FTAADTQSL |
|   | CLP-2473 | SLLEHFNTV |
|   | CLP-2474 | STIKEEPKI |
|   | CLP-2475 | KIDFRVYNL |
|   | CLP-2476 | NLLTPDSKM |
|   | CLP-2477 | KMGEPVSES |
|   | CLP-2478 | GLKEKVWTE |
|   | CLP-2479 | VTWRGADIL |
|   | CLP-2480 | ILRGSPSYT |
| 7 | CLP-2481 | YTQASLGLL |
|   | CLP-2482 | ASLGLLTPV |
|   | CLP-2483 | GLLTPVSGT |
|   | CLP-2484 | GTQEQTKTL |
|   | CLP-2485 | KTLRDSPNV |
|   | CLP-2486 | HLARPIYGL |
|   | CLP-2487 | PIYGLAVET |
|   | CLP-2488 | LAVETKGFL |
|   | CLP-2489 | FLQGAPAGG |
|   | CLP-2490 | AGGEKSGAL |
| 8 | CLP-2491 | GALPQQYPA |
|   | CLP-2492 | ALPQQYPAS |
|   | CLP-2493 | FCANCLTTK |
|   | CLP-2494 | ANGGYVCNA |
|   | CLP-2495 | NACGLYQKL |

-continued

| PEPTIDE GROUP | PEPTIDE NUMBER | SEQUENCE |
|---|---|---|
| | CLP-2496 | GLYQKLHST |
| | CLP-2497 | KLHSTPRPL |
| | CLP-2498 | STPRPLNII |
| | CLP-2499 | RLNPEALQA |
| | CLP-2500 | VLVSQTLDI |
| 9 | CLP-2501 | DIHKRMQPL |
| | CLP-2502 | RMQPLHIQI |
| | CLP-2503 | YPLFGLPFV |
| | CLP-2504 | GLPFVHNDF |
| | CLP-2505 | FVHNDFQSE |
| | CLP-2506 | SVPGNPHYL |
| | CLP-2507 | GNPHYLSHV |
| | CLP-2508 | HYLSHVPGL |
| | CLP-2509 | YVPYPTFNL |
| | CLP-2510 | FNLPPHFSA |
| 10 | CLP-2511 | NLPPHFSAV |
| | CLP-2512 | SAVGSDNDI |
| | CLP-2513 | KNEGPLNVV |
| | CLP-2514 | TKCVHCGIV |
| | CLP-2515 | CVHCGIVFL |
| | CLP-2516 | CGIVFLDEV |
| | CLP-2517 | FLDEVMYAL |
| | CLP-2518 | VMYALHMSC |
| | CLP-2519 | FQCSICQHL |
| | CLP-2520 | GLHRNNAQV |

2. Immune Reactivity of BFA4 Peptides and Generation of Human Effector T cells:

The BFA4 peptides were grouped into different pools of 7-10 peptides for immunological testing. Dissolved peptide pools were pulsed onto autologous HLA-A*0201 dendritic cells and used to activate autologous T-cell-enriched PBMC preparations. Activated T cells from each peptide-pool-stimulated culture were re-stimulated another 3 to 5 times using CD40L-activated autologous B-cells. IFN-γ ELISPOT analysis and assays for CTL killing of peptide-pulsed target cells was performed to demonstrate the immunogenicity of these epitopes from BFA4.

Human T cells demonstrated effector cell activity against a number of pools of peptides from the BFA4 protein, as shown by their ability to secrete IFN-γ in ELISPOT assays. These experiments were repeated after different rounds of APC stimulation resulting in the same reactive peptide groups. Peptide groups 1, 2, 4, 5, 6, 7, 8, 9, and 10 were found to be immunoreactive in these assays. Subsequently, these reactive peptide groups were de-convoluted in additional IFN-γ ELISPOT assays in which single peptides from each group were tested separately. The individual peptides from BFA4 peptide groups 1, 5 6, 7, 8, 9, and 10 in ELISPOT assays. This analysis revealed a number of individual strongly reactive peptides from the BFA4 protein recognized by human T cells. It was also observed that many of these single peptides also induced CTL activity killing peptide-loaded human T2 lymphoma cell targets. These peptides are listed in Table VII:

TABLE VII

List of highly immunoreactive peptides from BFA4

| Strong IFN-γ Killing | | Strong CTL Killing | |
|---|---|---|---|
| CLP 2425 | RNMLAFSFP | CLP 2425 | RNMLAFSFP |
| CLP 2426 | NMLAFSFPA | CLP 2426 | NMLAFSFPA |
| CLP 2427 | MLAFSFPAA | CLP 2427 | MLAFSFPAA |
| CLP 2461 | HLGEITYPF | | |
| CLP 2468 | FTTPDVDVL | CLP 2468 | FTTPDVDVL |
| CLP 2470 | VLLFHYYESV | CLP 2470 | VLLFHYYESV |
| CLP 2474 | KIDFRVYNL | | |
| CLP 2482 | ASLGLLTPV | CLP 2482 | ASLGLLTPV |
| CLP 2486 | HLARPIYGL | CLP 2486 | HLARPIYGL |
| CLP 2495 | NACGLYQKL | CLP 2495 | NACGLYQKL |
| CLP 2497 | KLHSTPRPL | | |
| CLP 2499 | RLNPEALQA | CLP 2499 | RLNPEALQA |
| CLP 2503 | YPLFGLPFV | | |
| CLP 2509 | YVPYPTFNL | CLP 2509 | YVPYPTFNL |
| CLP 2511 | NLPPHFSAV | | |
| CLP 2518 | VMYALHMSC | | |
| CLP 2520 | GLHRNNAQV | CLP 2520 | GLHRNNAQV |

D. Immune Responses Against BFA4 After Immunization In Vivo:

The pcDNA3.1/Zeo-BFA4 plasmid was used to immunize transgenic mice expressing a hybrid HLA-A*0201 α1α2 domain fused to a murine Kb α3 domain in C57BL/6 mice (A2-Kb mice). IFN-γ ELISPOT analysis using the groups of pooled peptides after DNA immunization and removal of activated spleen cells revealed a number of reactive BFA4 peptide groups. Some of these groups (especially group 7 and 8) also reacted strongly in human T-cell cultures suggesting that overlapping groups of peptides are recognized by human T cells and are naturally processed and presented on HLA-A2 after vaccination.

Vaccination experiments were also performed with the NYVAC-BFA4 and the MP76-18-BFA4 vectors in A2-Kb mice. Mice were immunized subcutaneously with 10-20 μg of MP-76-18-BFA4 and $1-2 \times 10^7$ pfu vP2033 (NYVAC-BFA4) and boosted 28 days later with the same amounts of each vector. Re-stimulation of spleen cells from the immunized mice with the pools of BFA4 peptides revealed induction of IFN-γ production in response to BFA4 peptide groups 2, 3, 4, 5, 7, 9, and 10 in ELISPOT assays. Thus, the BFA4 gene encoded in a CMV promoter driven eukaryotic plasmid, NYVAC, or a Semliki replicase-based DNA plasmid, were all capable of inducing T-cell responses against the BFA4 protein in vivo.

Example 2

BCY1 Tumor Antigen

The BCY1 gene was detected as a partial open reading frame (ORF) homologous to a nematode gene called "posterior-expressed maternal gene-3" (PEM-3) playing a role in posterior to anterior patterning in *Caenorhabtidis elegans* embryos. No previous involvement of this gene in cancer has been documented.

A. BCY1 and Amino Acid DNA Sequences

A partial DNA sequence was originally determined for BCY1. Primers, 9616SXC and 9617SXC, are derived from the BCY I partial DNA sequence and are designed to clone BCY I by RT-PCR from Calu 6 total RNA. The primers were designed such that the PCR product has BamHI sites at both ends and an ATG start codon and a Kozak sequence at the 5' end, as shown below:

```
9616SXC:   5' CAGTACGGATCCACCATGGCCGAGCTGCGCCTGA
              AGGGC 3'

9617SXC:   5' CCACGAGGATCCTTAGGAGAATATTCGGATGGC
              TTGCG 3'
```

The 1.2 Kb expected amplicon was obtained using ThermoScript RT-PCR System (Invitrogen) under optimized conditions. The PCR products from three separate RT-PCR's were digested with BamHI and respectively inserted in pcDNA3. 1/Zeo(+). The resulting clones were MC50A6, MC50A8 and MC50A19 from the first RT-PCR; MC54.21 from the second RT-PCR and MC55.29; and, MC55.32 from the third RT-PCR (FIG. 3). The following primers were utilized in sequencing the clones:

```
9620MC:    5' TAATACGACTCACTATAGGG 3'

9621MC:    5' TAGAAGGCACAGTCGAGG 3'

9618MC:    5' GAAAACGACTTCCTGGCGGGAG 3'

9619MC:    5' GCTCACCCAGGCGTGGGCCTC 3'
```

Figure 3B:
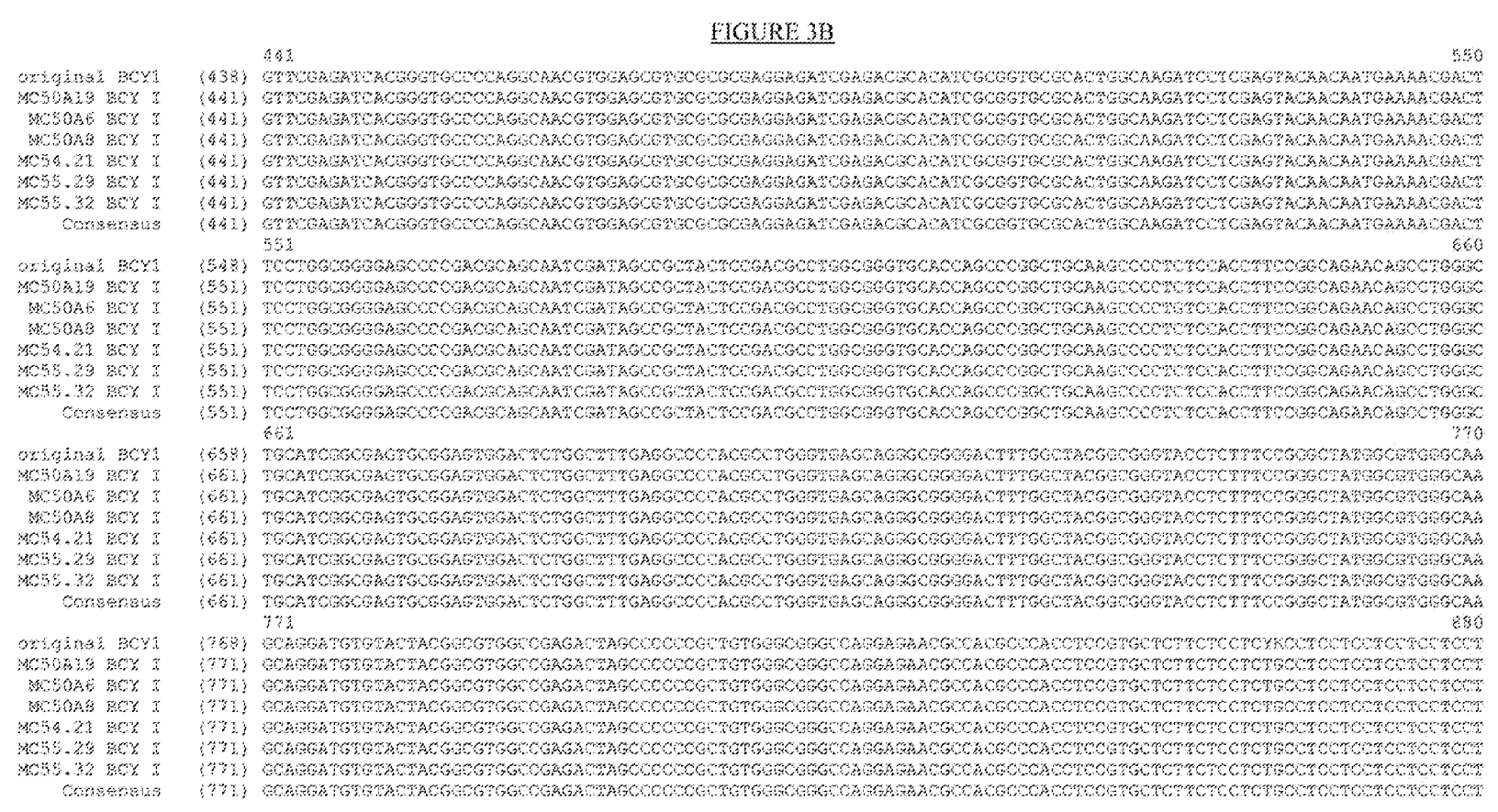
Figure 3C:
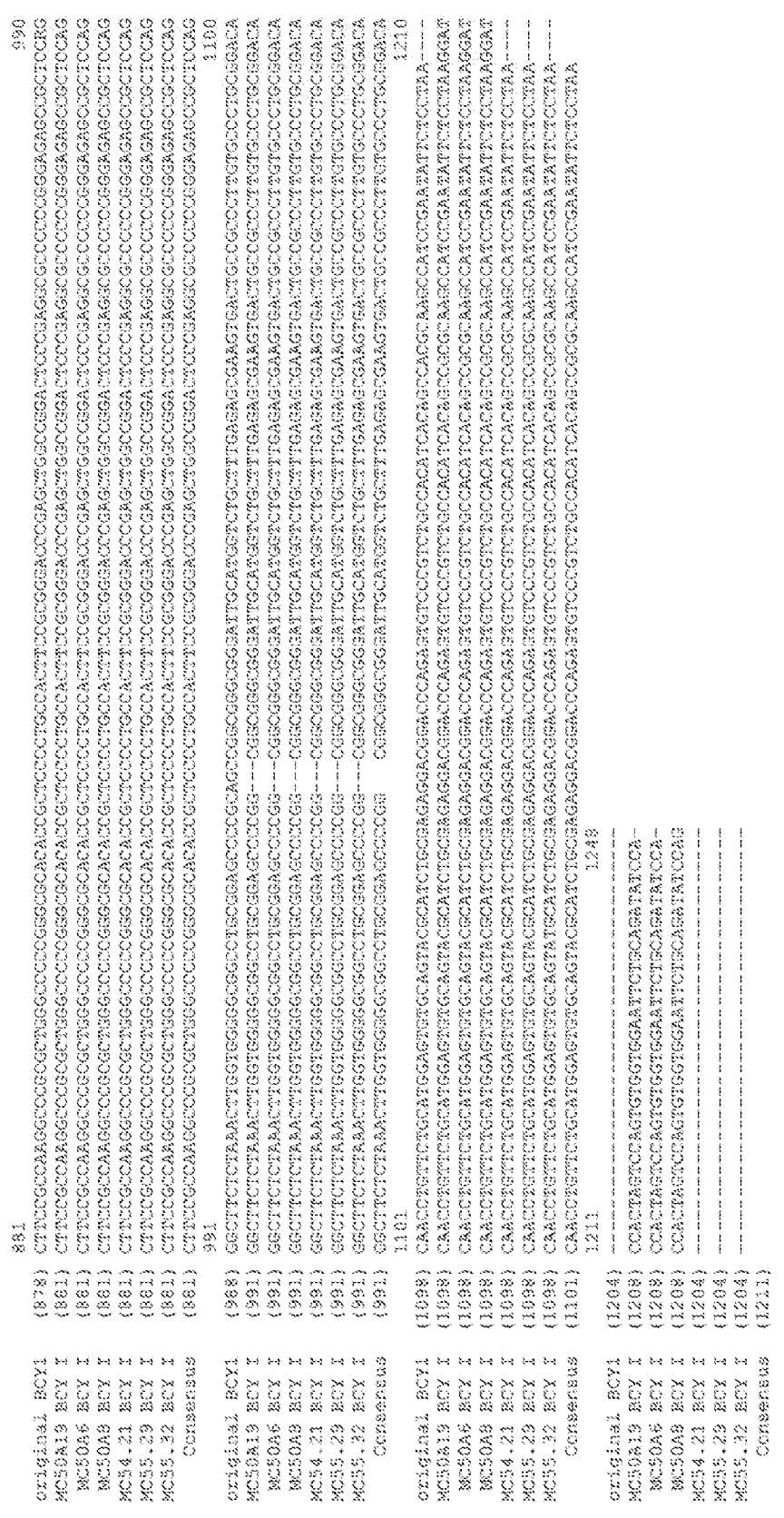

DNA sequencing of all six clones indicated a consensus sequence, as shown in FIGS. 3A, and B, C, and D having the following differences from the original partial BCY1 sequence: a C to G substitution at position 1031 resulting in an amino acid change of Ala to Gly; a GC deletion at position 1032-1034 resulting in a Thr deletion; and, an A to G substitution at position 1177 resulting in an amino acid change of Thr to Ala. Clones MC50A8 and MC55.29 are identical to the consensus sequence. The amino acid sequence of BCY1 is shown in FIG. 3D.

B. Immunological Reagents for BCY1 Breast Cancer Antigen:

A library of 100 nonamer peptides spanning the BCY1 gene product was synthesized. The peptides were chosen based on their potential ability to bind to HLA-A*0201. Table VIII lists 100 nonamer peptide epitopes for HLA-A*0201 from the BCY1 protein tested (see below):

TABLE VIII

| Peptide Designation | Sequence | Position in Protein |
|---|---|---|
| *CLP-2599 | VPVPTSEHV | 2 |
| *CLP-2602 | PTSEHVAEI | 5 |
| *CLP-2609 | EIVGRQCKI | 12 |
| *CLP-2616 | KIKALRAKT | 19 |
| *CLP-2618 | KALRAKTNT | 21 |
| *CLP-2619 | ALRAKTNTY | 22 |
| *CLP-2620 | LRAKTNTYI | 23 |

TABLE VIII-continued

| Peptide Designation | Sequence | Position in Protein |
|---|---|---|
| *CLP-2624 | TNTYIKTPV | 27 |
| *CLP-2627 | YIKTPVRGE | 30 |
| *CLP-2630 | TPVRGEEPV | 33 |
| *CLP-2633 | RGEEPVFMV | 36 |
| *CLP-2640 | MVTGRREDV | 43 |
| CLP-2641 | VTGRREDVA | 44 |
| *CLP-2643 | GRREDVATA | 46 |
| CLP-2647 | DVATARREI | 50 |
| CLP-2648 | VATARREII | 51 |
| *CLP-2650 | TARREIISA | 53 |
| *CLP-2651 | ARREIISAA | 54 |
| *CLP-2655 | IISAAEHFS | 58 |
| *CLP-2656 | ISAAEHFSM | 59 |
| CLP-2657 | SAAEHFSMI | 60 |
| *CLP-2659 | AEHFSMIRA | 62 |
| *CLP-2663 | SMIRASRNK | 66 |
| CLP-2666 | RASRNKSGA | 69 |
| *CLP-2670 | NKSGAAFGV | 73 |
| *CLP-2673 | GAAFGVAPA | 76 |
| *CLP-2674 | AAFGVAPAL | 77 |
| *CLP-2677 | GVAPALPGQ | 80 |
| *CLP-2678 | VAPALPGQV | 81 |
| *CLP-2680 | PALPGQVTI | 83 |
| *CLP-2681 | ALPGQVTIR | 84 |
| *CLP-2682 | LPGQVTIRV | 85 |
| CLP-2684 | GQVTIRVRV | 87 |
| *CLP-2689 | RVRVPYRVV | 92 |
| *CLP-2691 | RVPYRVVGL | 94 |
| *CLP-2692 | VPYRVVGLV | 95 |
| *CLP-2695 | RVVGLVVGP | 98 |
| *CLP-2698 | GLVVGPKGA | 101 |
| *CLP-2699 | LVVGPKGAT | 102 |
| *CLP-2700 | VVGPKGATI | 103 |
| *CLP-2710 | RIQQQTNTY | 113 |
| *CLP-2711 | IQQQTNTYI | 114 |
| *CLP-2712 | QQQTNTYII | 115 |
| *CLP-2713 | QQTNTYIIT | 116 |
| *CLP-2718 | YIITPSRDR | 121 |

TABLE VIII-continued

| Peptide Designation | Sequence | Position in Protein |
|---|---|---|
| CLP-2721 | TPSRDRDPV | 124 |
| CLP-2724 | RDRDPVFEI | 127 |
| CLP-2731 | EITGAPGNV | 134 |
| CLP-2734 | GAPGNVERA | 137 |
| CLP-2738 | NVERAREEI | 141 |
| CLP-2744 | EEIETHIAV | 147 |
| CLP-2746 | IETHIAVRT | 149 |
| CLP-2749 | HIAVRTGKI | 152 |
| CLP-2750 | IAVRTGKIL | 153 |
| CLP-2756 | KILEYNNEN | 159 |
| CLP-2760 | YNNENDFLA | 163 |
| CLP-2762 | NENDFLAGS | 165 |
| CLP-2766 | FLAGSPDAA | 169 |
| CLP-2767 | LAGSPDAAI | 170 |
| CLP-2774 | AIDSRYSDA | 177 |
| CLP-2777 | SRYSDAWRV | 180 |
| CLP-2785 | VHQPGCKPL | 188 |
| CLP-2793 | LSTFRQNSL | 196 |
| CLP-2801 | LGCIGECGV | 204 |
| CLP-2807 | CGVDSGFEA | 210 |
| CLP-2812 | GFEAPRLDV | 215 |
| CLP-2817 | RLDVYYGVA | 220 |
| CLP-2819 | DVYYGVAET | 222 |
| CLP-2823 | GVAETSPPL | 226 |
| CLP-2825 | AETSPPLWA | 228 |
| CLP-2830 | PLWAGQENA | 233 |
| CLP-2833 | AGQENATPT | 236 |
| CLP-2835 | QENATPTSV | 238 |
| CLP-2843 | VLFSSASSS | 246 |
| CLP-2857 | KARAGPPGA | 260 |
| CLP-2869 | PATSAGPEL | 272 |
| CLP-2870 | ATSAGPELA | 273 |
| CLP-2872 | SAGPELAGL | 275 |
| CLP-2879 | GLPRRPPGE | 282 |
| CLP-2887 | EPLQGFSKL | 290 |
| CLP-2892 | FSKLGGGGL | 295 |
| CLP-2894 | KLGGGGLRS | 297 |
| CLP-2899 | GLRSPGGGR | 302 |
| CLP-2909 | CMVCFESEV | 312 |
| CLP-2910 | MVCFESEVT | 313 |
| CLP-2911 | VCFESEVTA | 314 |
| CLP-2913 | FESEVTAAL | 316 |
| CLP-2916 | EVTAALVPC | 319 |
| CLP-2917 | VTAALVPCG | 320 |
| CLP-2920 | ALVPCGHNL | 323 |
| CLP-2921 | LVPCGHNLF | 324 |
| CLP-2922 | VPCGHNLFC | 325 |
| CLP-2927 | NLFCMECAV | 330 |
| CLP-2929 | FCMECAVRI | 332 |
| CLP-2933 | CAVRICERT | 336 |
| CLP-2936 | RICERTDPE | 339 |
| CLP-2940 | RTDPECPVC | 343 |
| CLP-2945 | CPVCHITAT | 348 |
| CLP-2947 | VCHITATQA | 350 |
| CLP-2950 | ITATQAIRI | 353 |

TABLE IX shows the groups of peptides used for immunological testing:

| Peptide Group | Peptide Number | Peptide Sequence |
|---|---|---|
| 1 | CLP 2887 | EPLQGFSKL |
|   | CLP 2916 | EVTAALVPC |
|   | CLP 2945 | CPVCHITAT |
|   | CLP 2673 | KIKALRAKT |
|   | CLP 2699 | IISAAEHFS |
|   | CLP 2616 | RASRNKSGA |
|   | CLP 2655 | GAAFGVAPA |
|   | CLP 2731 | LVVGPKGAT |
|   | CLP 2734 | EITGAPGNV |
|   | CLP 2666 | GAPGNVERA |
| 2 | CLP 2724 | ALRAKTNTY |
|   | CLP 2689 | VATARREII |
|   | CLP 2648 | PALPGQVTI |
|   | CLP 2680 | ALPGQVTIR |
|   | CLP 2619 | RVRVPYRVV |
|   | CLP 2681 | RDRDPVFEI |
|   | CLP 2689 | RVRVPYRVV |
|   | CLP 2947 | HIAVRTGKI |
|   | CLP 2762 | NENDFLAGS |
|   | CLP 2933 | CAVRICERT |
|   | CLP 2749 | VCHITATQA |
| 3 | CLP 2647 | GRREDVATA |
|   | CLP 2677 | DVATARREI |
|   | CLP 2643 | TARREIISA |
|   | CLP 2785 | GVAPALPGQ |
|   | CLP 2917 | RVVGLVVGP |
|   | CLP 2695 | VHQPGCKPL |
|   | CLP 2650 | PATSAGPEL |
|   | CLP 2869 | VTAALVPCG |
| 4 | CLP 2812 | VPVPTSEHV |
|   | CLP 2892 | ARREIISAA |
|   | CLP 2738 | RIQQQTNTY |

TABLE IX-continued shows the groups of peptides used for immunological testing:

| Peptide Group | Peptide Number | Peptide Sequence |
|---|---|---|
|   | CLP 2651 | NVERAREEI |
|   | CLP 2870 | GFEAPRLDV |
|   | CLP 2899 | ATSAGPELA |
|   | CLP 2710 | FSKLGGGGL |
|   | CLP 2599 | GLRSPGGGR |
| 5 | CLP 2609 | PTSEHVAEI |
|   | CLP 2602 | EIVGRQCKI |
|   | CLP 2641 | LRAKTNTYI |
|   | CLP 2620 | VTGRREDVA |
|   | CLP 2940 | SMIRASRNK |
|   | CLP 2921 | CMVCFESEV |
|   | CLP 2936 | LVPCGHNLF |
|   | CLP 2663 | NLFCMECAV |
|   | CLP 2927 | RICERTDPE |
|   | CLP 2909 | RTDPECPVC |
| 6 | CLP 2766 | MVTGRREDV |
|   | CLP 2711 | GLVVGPKGA |
|   | CLP 2913 | IQQQTNTYI |
|   | CLP 2823 | FLAGSPDAA |
|   | CLP 2640 | GVAETSPPL |
|   | CLP 2698 | FESEVTAAL |
|   | CLP 2929 | FCMECAVRI |
| 7 | CLP 2760 | KALRAKTNT |
|   | CLP 2633 | RGEEPVFMV |
|   | CLP 2700 | SAAEHFSMI |
|   | CLP 2835 | AAFGVAPAL |
|   | CLP 2618 | VVGPKGATI |
|   | CLP 2657 | YNNENDFLA |
|   | CLP 2674 | LGCIGECGV |
|   | CLP 2911 | QENATPTSV |
|   | CLP 2801 | VCFESEVTA |
| 8 | CLP 2807 | TNTYIKTPV |
|   | CLP 2872 | NKSGAAFGV |
|   | CLP 2670 | QQTNTYIIT |
|   | CLP 2756 | KILEYNNEN |
|   | CLP 2825 | CGVDSGFEA |
|   | CLP 2843 | AETSPPLWA |
|   | CLP 2713 | PLWAGQENA |
|   | CLP 2624 | VLFSSASSS |
|   | CLP 2830 | SAGPELAGL |
| 9 | CLP 2712 | ISAAEHFSM |
|   | CLP 2744 | QQQTNTYII |
|   | CLP 2774 | EEIETHIAV |
|   | CLP 2819 | IETHIAVRT |
|   | CLP 2656 | LAGSPDAAI |
|   | CLP 2922 | AIDSRYSDA |
|   | CLP 2746 | DVYYGVAET |
|   | CLP 2767 | VPCGHNLFC |
|   | CLP 2950 | ITATQAIRI |
| 10 | CLP 2793 | TPVRGEEPV |

TABLE IX-continued shows the groups of peptides used for immunological testing:

| Peptide Group | Peptide Number | Peptide Sequence |
|---|---|---|
|   | CLP 2777 | AEHFSMIRA |
|   | CLP 2910 | VAPALPGQV |
|   | CLP 2721 | TPSRDRDPV |
|   | CLP 2630 | IAVRTGKIL |
|   | CLP 2659 | SRYSDAWRV |
|   | CLP 2678 | LSTFRQNSL |
|   | CLP 2750 | RLDVYYGVA |
|   | CLP 2833 | AGQENATPT |
|   | CLP 2817 | MVCFESEVT |

C. Immune Reactivity of BCY1 Peptides and Generation of Human Effector T Cells:

The library of 100 peptides from BCY1 was separated into 10 groups of 7-10 peptides for immunological testing. Dissolved peptide pools were pulsed onto autologous HLA-A*0201 dendritic cells and used to activate autologous T-cell-enriched PBMC preparations. Activated T cells from each peptide-pool-stimulated culture were re-stimulated another 3 to 5 times using CD40L-activated autologous B-cells. IFN-γ ELISPOT analysis and assays for CTL killing of peptide-pulsed target cells was performed to demonstrate the immunogenicity of these epitopes from BCY1.

Human T cells demonstrated effector cell activity against a number of pools of peptides from the BCY1 protein, as shown by their ability to secrete IFN-γ in ELISPOT assays. These experiments were repeated after different rounds of APC stimulation resulting in the same reactive peptide groups. Peptide groups 1, 2, 3, 4, 5, 6, and 7 were found to be immunoreactive in these assays. Subsequently, these reactive peptide groups were de-convoluted in additional IFN-γ ELISPOT assays in which single peptides from each group were tested separately. This analysis revealed a number of individual strongly reactive peptides from the BCY1 protein recognized by human T cells. Many of these single peptides also induced CTL activity killing peptide-loaded human T2 lymphoma cell targets. Table IX lists these peptides.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A poxvirus expression vector for expressing the BFA4 protein in a cell, the vector comprising the nucleic acid sequence of SEQ ID NO.: 1 and at least one nucleic sequence encoding an angiogenesis-associated antigen, wherein administration of the vector to a mammal induces a T-cell response against the BFA4 protein.

2. The expression vector of claim 1 further comprising at least one additional tumor-associated antigen.

3. The expression vector of claim 2 wherein the poxvirus is selected from the group consisting of vaccinia, NYVAC, avipox, canarypox, ALVAC, ALVAC(2), fowlpox, and TROVAC.

4. The expression vector of claim 3 wherein the poxvirus is selected from the group consisting of NYVAC, ALVAC, and ALVAC(2).

5. The expression vector of claim 1 wherein the poxvirus is selected from the group consisting of vaccinia, NYVAC, avipox, canarypox, ALVAC, ALVAC(2), fowlpox, and TROVAC.

6. The expression vector of claim 5 wherein the poxvirus is selected from the group consisting of NYVAC, ALVAC, and ALVAC(2).

7. The expression vector of claim 1 further comprising at least one nucleic acid sequence encoding a co-stimulatory component.

8. The expression vector of claim 7 wherein the poxvirus is selected from the group consisting of vaccinia, NYVAC, avipox, canarypox, ALVAC, ALVAC(2), fowlpox, and TROVAC.

9. The poxvirus of claim 8 wherein the poxvirus is selected from the group consisting of NYVAC, ALVAC, and ALVAC(2).

10. A composition comprising the poxvirus expression vector of claim 1 and a pharmaceutically acceptable carrier.

11. The composition of claim 10 wherein the poxvirus is selected from the group consisting of vaccinia, NYVAC, avipox, canarypox, ALVAC, ALVAC(2), fowlpox, and TROVAC.

12. The composition of claim 11 wherein the poxvirus is selected from the group consisting of NYVAC, ALVAC, and ALVAC(2).

13. The expression vector of claim 2 wherein the at least one additional tumor-associated antigen has the amino acid sequence of SEQ ID NO:4.

14. The expression vector of claim 2 further comprising at least one nucleic acid sequence encoding a co-stimulatory component.

15. A composition comprising the poxvirus expression vector of claim 2 and a pharmaceutically acceptable carrier.

16. The composition of claim 15 wherein the poxvirus is selected from the group consisting of vaccinia, NYVAC, avipox, canarypox, ALVAC, ALVAC(2), fowlpox, and TROVAC.

17. The composition of claim 16 wherein the poxvirus is selected from the group consisting of NYVAC, ALVAC, and ALVAC(2).

18. A poxvirus expression vector comprising a nucleic acid sequence encoding a BFA4 protein having the amino acid sequence of SEQ ID NO:2 and at least one nucleic sequence encoding an angiogenesis-associated antigen, wherein administration of the vector to a mammal induces a T-cell response against the BFA4 protein.

19. The expression vector of claim 18 further comprising a nucleic acid encoding at least one additional tumor-associated antigen.

20. The expression vector of claim 19 wherein the poxvirus is selected from the group consisting of vaccinia, NYVAC, avipox, canarypox, ALVAC, ALVAC(2), fowlpox, and TROVAC.

21. The expression vector of claim 20 wherein the poxvirus is selected from the group consisting of NYVAC, ALVAC, and ALVAC(2).

22. The expression vector of claim 18 wherein the poxvirus is selected from the group consisting of vaccinia, NYVAC, avipox, canarypox, ALVAC, ALVAC(2), fowlpox, and TROVAC.

23. The expression vector of claim 22 wherein the poxvirus is selected from the group consisting of NYVAC, ALVAC, and ALVAC(2).

24. The expression vector of claim 18 further comprising at least one nucleic acid sequence encoding a co-stimulatory component.

25. The expression vector of claim 24 wherein the poxvirus is selected from the group consisting of vaccinia, NYVAC, avipox, canarypox, ALVAC, ALVAC(2), fowlpox, and TROVAC.

26. The poxvirus of claim 25 wherein the poxvirus is selected from the group consisting of NYVAC, ALVAC, and ALVAC(2).

27. A composition comprising an expression vector of claim 19 and a pharmaceutically acceptable carrier.

28. A composition comprising an expression vector of claim 18 and a pharmaceutically acceptable carrier.

29. The expression vector of claim 7, 24, or 14 wherein the co-stimulatory component is B7.1.

30. The expression vector of claim 7, 24, or 14 wherein the co-stimulatory component is TRICOM comprising B7.1, LFA-3 and ICAM-1.

31. The expression vector of claim 1 or 18 wherein the angiogenesis-associated antigen is selected from the group consisting of vascular endothelial growth factor, vascular endothelial growth factor receptor EPH receptors, epidermal growth factor receptor, basic fibroblast growth factor, platelet-derived cell growth factor, platelet-derived endothelial cell growth factor, a transforming growth factor, endoglin, an Id proteins, uPA, uPAR, a matrix metalloproteinases, thrombospondin, and surface proteolglycan NG2.

32. The expression vector claim 2 or 19 wherein the at least one additional tumor-associated antigen is selected from the group consisting of gp100, TRP-1, NY-ESO-1, a MAGE antigen, MAGE-1, MAGE-3, carcinoembryonic antigen, MUC-1, and NY-BR-1.

* * * * *